US010260953B2

(12) United States Patent
Engelbart et al.

(10) Patent No.: US 10,260,953 B2
(45) Date of Patent: Apr. 16, 2019

(54) APPLIQUE AND METHOD FOR THERMOGRAPHIC INSPECTION

(71) Applicant: THE BOEING COMPANY, Chicago, IL (US)

(72) Inventors: Roger W. Engelbart, St. Louis, MO (US); Nathan R. Smith, St. Charles, MO (US); Loyal B. Shawgo, O'Fallon, MO (US)

(73) Assignee: The Boeing Company, Chicago, IL (US)

( * ) Notice: Subject to any disclaimer, the term of this patent is extended or adjusted under 35 U.S.C. 154(b) by 177 days.

(21) Appl. No.: 15/235,024

(22) Filed: Aug. 11, 2016

(65) Prior Publication Data

US 2018/0045574 A1  Feb. 15, 2018

(51) Int. Cl.
*G01J 5/00* (2006.01)
*G01J 5/08* (2006.01)
*G01N 21/88* (2006.01)

(52) U.S. Cl.
CPC ............ *G01J 5/0066* (2013.01); *G01J 5/0887* (2013.01); *G01J 5/0896* (2013.01); *G01N 21/8806* (2013.01); *G01J 2005/0077* (2013.01)

(58) Field of Classification Search
CPC ................ G01N 25/72; G01N 25/8806; G01J 2005/0077; G01J 2005/0081; G01J 5/0066; G01J 5/10; G01J 5/0003
USPC ............ 250/341.6, 338.1, 341.1, 341.8, 342, 250/559.42
See application file for complete search history.

(56) References Cited

U.S. PATENT DOCUMENTS

| 3,631,362 | A | * | 12/1971 | Almasi | H01S 3/042 372/35 |
| 4,352,142 | A | * | 9/1982 | Olson | H05F 3/00 361/117 |
| 4,854,724 | A | * | 8/1989 | Adams | G01N 25/72 374/124 |
| 4,866,276 | A | * | 9/1989 | Leavens | G01N 25/72 250/341.6 |
| 4,986,496 | A | * | 1/1991 | Marentic | B05D 5/02 244/130 |
| 5,111,048 | A | * | 5/1992 | Devitt | G01N 25/72 250/341.6 |
| 5,240,329 | A | * | 8/1993 | Zinkosky | G01N 25/72 250/330 |
| 5,567,950 | A | * | 10/1996 | Meeker | G01S 7/48 250/495.1 |

(Continued)

FOREIGN PATENT DOCUMENTS

CA  2 829 888 A1  7/2014

OTHER PUBLICATIONS

Usamentiaga, R. et al., "Infrared Thermography for Temperature Measurement and Non-Destructive Testing", 2014, Sensors 14(7), pp. 12305-12348.*

*Primary Examiner* — David P Porta
*Assistant Examiner* — Blake C Riddick
(74) *Attorney, Agent, or Firm* — Toler Law Group, PC

(57) ABSTRACT

A method of thermographic inspection includes absorbing, at an applique applied to a test area of an article, light from a testing light source. The method further includes emitting, by the applique, thermal radiation directed to a capture device, the thermal radiation corresponding to at least a portion of the light absorbed by the applique.

20 Claims, 11 Drawing Sheets

(56) References Cited

U.S. PATENT DOCUMENTS

| | | | | |
|---|---|---|---|---|
| 5,576,710 A | * | 11/1996 | Broderick | H01Q 17/00 342/1 |
| 6,177,189 B1 | * | 1/2001 | Rawlings | C09J 7/22 428/343 |
| 6,198,098 B1 | * | 3/2001 | Laou | G01J 5/20 250/332 |
| 6,495,828 B1 | * | 12/2002 | Tidrow | G01J 5/34 250/338.1 |
| 6,531,699 B1 | * | 3/2003 | Micheron | G01J 1/06 250/332 |
| 6,790,526 B2 | * | 9/2004 | Vargo | B32B 7/12 428/343 |
| 7,407,136 B2 | * | 8/2008 | Murg | B64C 7/00 244/1 R |
| 7,750,301 B1 | * | 7/2010 | Woolaway | G01J 5/02 250/339.09 |
| 8,726,737 B2 | | 5/2014 | Georgeson et al. | |
| 8,733,702 B1 | | 5/2014 | Rawlings et al. | |
| 9,006,857 B1 | * | 4/2015 | Carr | H01L 27/14601 257/12 |
| 9,490,292 B1 | * | 11/2016 | Yap | H01L 27/14652 |
| 2002/0030742 A1 | * | 3/2002 | Aman | A63B 24/0021 348/169 |
| 2002/0081921 A1 | * | 6/2002 | Vargo | B32B 15/08 442/16 |
| 2003/0011840 A1 | * | 1/2003 | Mitra | H01S 3/2383 398/79 |
| 2004/0021087 A1 | * | 2/2004 | Tokhtuev | G01J 1/02 250/372 |
| 2005/0056786 A1 | | 3/2005 | Shepard et al. | |
| 2005/0181203 A1 | | 8/2005 | Rawlings et al. | |
| 2008/0223152 A1 | * | 9/2008 | Georgeson | G01B 7/20 73/862.041 |
| 2009/0044744 A1 | * | 2/2009 | Koene | C08K 5/0041 116/207 |
| 2010/0193672 A1 | * | 8/2010 | Blasenheim | B01L 3/5025 250/234 |
| 2011/0281070 A1 | * | 11/2011 | Mittal | H01L 31/022466 428/142 |
| 2012/0070668 A1 | * | 3/2012 | Georgeson | B29C 65/4855 428/411.1 |
| 2012/0112165 A1 | * | 5/2012 | Charlton | H01L 27/14603 257/21 |
| 2012/0161005 A1 | * | 6/2012 | Tsuchiya | G01J 5/0225 250/338.3 |
| 2013/0098036 A1 | * | 4/2013 | Falcey | F03G 6/06 60/641.15 |
| 2013/0101776 A1 | * | 4/2013 | Lu | B32B 37/02 428/41.8 |
| 2013/0329054 A1 | * | 12/2013 | Hoelter | H04N 5/2252 348/164 |
| 2014/0184786 A1 | * | 7/2014 | Georgeson | G01N 21/8851 348/128 |
| 2014/0210997 A1 | * | 7/2014 | Blanchard | G01M 5/0016 348/128 |
| 2014/0295143 A1 | * | 10/2014 | Rawlings | B64C 23/005 428/168 |
| 2015/0153293 A1 | * | 6/2015 | Nosrati | G01N 25/72 374/5 |
| 2015/0198547 A1 | * | 7/2015 | Isakov | G01N 25/72 374/121 |
| 2016/0146665 A1 | * | 5/2016 | Silawan | G01J 5/047 250/349 |
| 2016/0178463 A1 | * | 6/2016 | Georgeson | G01P 15/06 116/201 |
| 2017/0166721 A1 | * | 6/2017 | Starkovich | C08J 9/35 |
| 2018/0011565 A1 | * | 1/2018 | Nekimken | G06F 3/044 |
| 2018/0045560 A1 | * | 2/2018 | Chanda | G01J 1/42 |
| 2018/0224330 A1 | * | 8/2018 | Yokino | G01J 3/18 |

* cited by examiner

APPLIQUE AND METHOD FOR THERMOGRAPHIC INSPECTION

GOVERNMENT LICENSE RIGHTS

This invention was made with Government support under FA8650-10-D-5210-024 awarded by Air Force Research Laboratory. The Government has certain rights in this invention.

FIELD OF THE DISCLOSURE

The present disclosure is generally related to appliques and methods for thermographic inspection.

BACKGROUND

Thermography inspection, such as infrared thermography inspection, is a nondestructive inspection method that is commonly utilized in field inspection of structures, such as aircraft structures. Thermography inspection utilizes the transfer of energy into an object of inspection to generate heat and detects heat energy (e.g., infrared light) that is dissipated from the object. In a particular example, thermography (e.g., infrared thermography) is used to inspect wing and stabilizer components that are fabricated from aluminum honeycomb which may be adhesively bonded between two aluminum or composite face sheets of varying thicknesses. A common defect to inspect for in such structures is a disbond, or separation of the aluminum honeycomb core from one of the two face sheets.

Depending on a particular technique (e.g., a one-side technique or a two-sided technique) of the thermography inspection, a disbond or other defect may appear as a "cool" spot or a "hot" spot. For example, when applying heat (e.g., light) to a first surface of a component of an aircraft, such as an airframe, and imaging a second surface of the component, a defect may appear as a "cool" spot. To illustrate, a lack of continuity in the component (e.g., in a frame or structure positioned between surfaces of the component) causes less heat to be transferred from the first surface to the second surface and causes less heat to be emitted from the second surface, which may be indicated as a cool spot in a thermographic image of the component relative to other portions of the component (e.g., defect free portions). As another example, when applying heat (e.g., light) to a surface of the component and imaging the same surface of the component, a disbond or other defect may appear as a "hot" spot. To illustrate, a lack of continuity in the component (e.g., in a frame or structure underlying the surface of the component) causes less heat to be transferred from the surface to a frame or structure that underlies the surface and causes more heat to be retained and emitted from the surface, which may be indicated as a hot spot in the thermographic image relative to other portions of the component.

Because thermography inspection often utilizes flashlamps to inject a heat generating energy pulse into the component, bare metal or very light colored surfaces of the component may reject incident energy and distort thermographic emitted infrared readings. In such situations, a majority of the light (e.g., heat) may be reflected by the component and therefore is not transfer into and absorbed by the component. Reflection of the light from a flashlamp may reduce the usefulness of a thermographic image of the component used to identify a location of a defect of the component. To reduce reflection of the light, a coating may be applied to a bare metal surface (or other surface) of the component to enable a more uniform heat transfer. Before applying the coating, the surface of the component of the aircraft is prepared by cleaning the surface, and after performance of a thermographic inspection, the surface of the component is cleaned (e.g., using a solvent) before the aircraft is ready for use.

Different coatings may be used as part of the thermographic inspection process. However, coatings may be applied non-uniformly, causing variations in heat transfer into the part and infrared emission from the part. Additionally, an overly thick coating may act as an insulator. To illustrate, an overly thick coating may impede heat transfer into the part, may impede infrared emission from the part, or both. As a particular example, the coating may include flat black paint. The flat black paint may be a water-soluble tempera that is applied to a surface of the component by spraying or brushing. A thermographic inspection may begin after the flat black paint has dried, which increases an amount of time associated with preparing for and performing the thermographic inspection. Additionally, the flat black paint coating is prone to scratches that may occur when a thermographic image capture device contacts the coated surface of the component during thermographic inspection process. The scratches may generate visual interference and may reduce detection of small flaws during analysis of a captured thermographic image of the component.

As another particular example, the coating may include a layer of lampblack coating. The lampblack coating is carbon black (e.g., a black pigment made from soot or other fine carbon powder) with a solvent carrier, such as an aerosol product. While application of the lampblack coating is faster than application of the flat black paint, the application of the lampblack coating is messy and often results in overspray. Additionally, an amount of time spent cleaning the component after the thermographic inspection is complete may be longer than an amount of time to remove the flat black paint. Thus, with current thermography techniques (e.g., using the flat black paint or the lampblack coating) surface preparation and cleaning account for a significant portion of the thermographic inspection process.

SUMMARY

In a particular implementation, a method of thermographic inspection includes absorbing, at an applique applied to a test area of an article, light from a testing light source. The method further includes emitting, by the applique, thermal radiation directed to a capture device, the thermal radiation corresponding to at least a portion of the light absorbed by the applique.

In some implementations, an applique includes a first surface that includes a thermally conductive material and a second surface defining a plurality of light absorbing cavities, where at least a portion of the second surface opposes the first surface.

In another particular implementation, an applique includes a first surface that includes a thermally conductive material and a second surface that includes a plurality of microstructures extending from the second surface. At least a portion of the second surface opposes the first surface. The second surface has a light absorption coefficient that is greater than a light reflection coefficient of the second surface.

By utilizing an applique, such as a removable or reusable applique, in place of spray or brush coatings for thermography inspection, surface preparation and cleaning time may be reduced. By reducing surface preparation and cleaning time, inspection times may are shortened and cost savings may be achieved. By including a plurality of surface features (e.g., cavities, microstructures, nanoparticles, etc.) in the applique, the applique may provide higher quality thermographic images than conventional planar or colorized appliques. For example, the plurality of surface features may increase absorptivity and emissivity of the applique and may decrease reflectivity. Accordingly, a signal to noise ratio of the thermographic images may be increased which may result in higher quality thermographic images that enable an increased detection of defects in an article.

DETAILED DESCRIPTION

Figure 1:
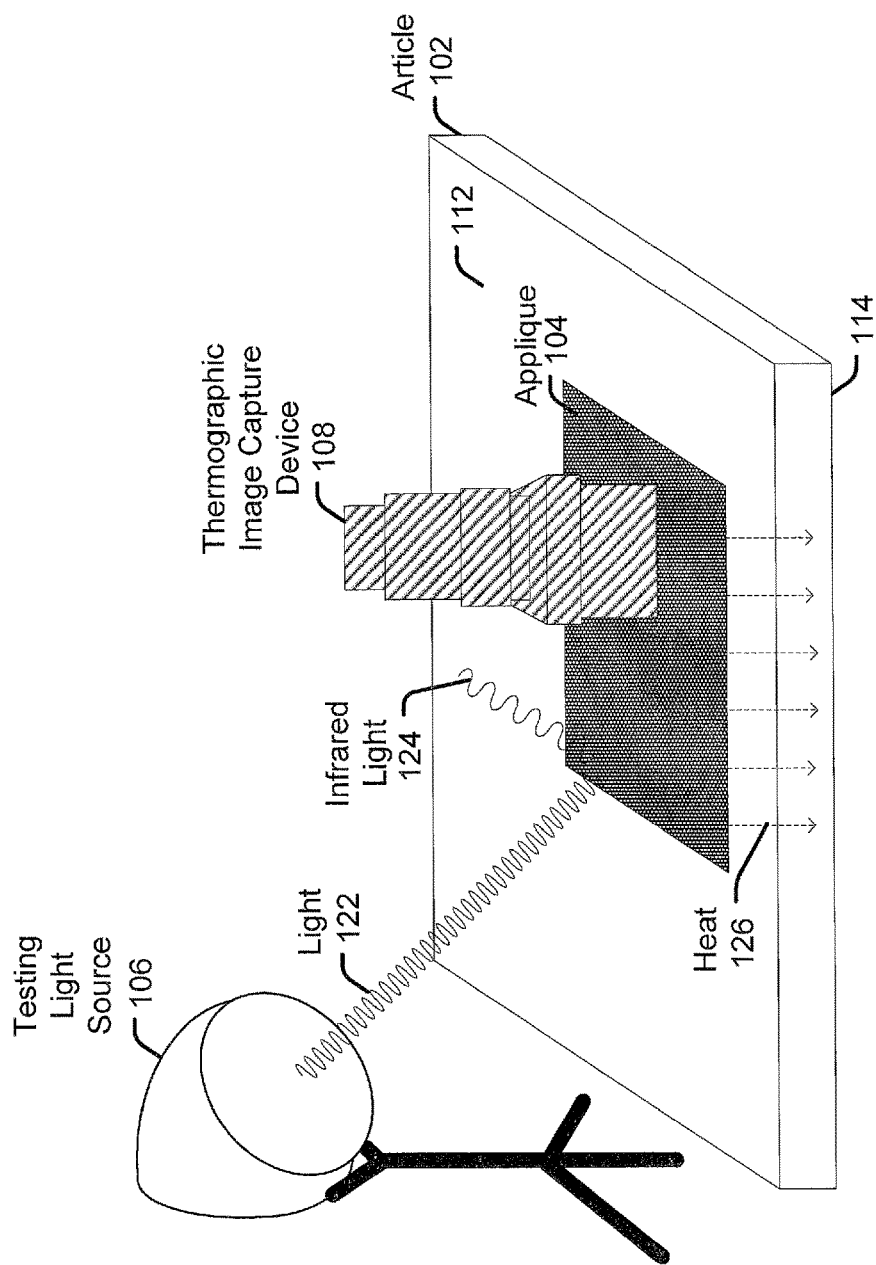
FIG. 1 is a diagram that illustrates an example of a thermographic inspection system including an applique.

Implementations disclosed herein enable non-destructive inspection of articles, such as components of an aircraft. In particular, an applique may be affixed to an article and a thermographic inspection may be performed to examine the article for structural and sub-surface defects. In some implementations, the applique may be removable and reusable. Thermography involves capturing infrared light indicative of a heat distribution of an object. Thermographic inspection involves evaluating the heat distribution (e.g., temperature differences between areas of the object) to indicate structural or sub-surface defects in the article. To illustrate, a structural or sub-surface defect may impair heat transfer (e.g., conduction of thermal energy) between a surface and the structure of an article. As another example, a structural or sub-surface defect may impair conduction of thermal energy between a first surface and a second surface of an article.

When heat is applied to the surface, such as by electromagnetic radiation (e.g., light), hot spots (e.g., areas of increased temperature) may be detected on the surface above the structural or sub-surface defect as less heat may be transferred to the article. To illustrate, less heat may be conducted to the structure of the article or penetrate the article because of a defect in the structure or the sub-surface. These hot spots may emit a greater amount of thermal radiation as compared to the rest of the surface, and this difference in thermal radiation may be captured by a thermographic image capture device. Accordingly, the thermographic image capture device may indicate a potential structural or sub-surface defect. As an illustrative, non-limiting example, thermographic inspection may detect a disbond between an aluminum honeycomb core structure and an aluminum face sheet of a component of an aircraft.

In a particular implementation, an applique may be applied to a surface of an article to be tested for structural or sub-surface defects. For example, a first surface of an applique may be applied to at least a portion of a surface (e.g., a test area) of the article. The first surface of the applique may be applied via surface tension, static electricity, or an adhesive, as illustrative, non-limiting examples. The applique may be removable and thermally conductive. Light (e.g., a light pulse) from a testing light source may be directed at a second surface of the applique. At least a portion of the second surface opposes the first surface. For example, the second surface may be an opposite surface of the applique as compared to the first surface. The second surface of the applique may absorb a portion of the light (e.g., thermal energy) and the applique may increase in temperature. As an illustrative, non-limiting example, the second surface of the applique may have a matte black finish. The applique may transfer a first portion of the thermal energy from the first surface to the article by conduction and may emit a second portion of the thermal energy as thermal radiation (e.g., infrared light) by radiation. The thermal radiation may be captured by a thermographic image capture device. When a potential structural or sub-surface defect is present in the article, the first portion of the thermal energy may be lower for an area corresponding to the potential structural or sub-surface defect. Accordingly, the second portion of the thermal energy emitted as thermal radiation may be greater for the area corresponding to the potential structural or sub-surface defect. Thus, the thermal radiation captured by the thermographic image capture device may vary across the second surface of the applique and the greater thermal energy emitted by the area corresponding to the potential defect may produce a hot spot as compared to other areas of the applique. The hot spot may be indicative of a potential structural or sub-surface defect.

Additionally, the second surface of the applique may include features that may increase an amount of the light absorbed and an amount of the thermal radiation emitted. As an example, the second surface of the applique may define a plurality of light absorbing cavities. As another example, a plurality of microstructures may extend from the second surface and the plurality of microstructures may direct light towards the second surface, may absorb the light, or both. Furthermore, the thermographic inspection system (e.g., the thermographic image capture device and the testing light source) may be computer-controllable or automated. For example, a user may control the thermographic inspection system (or a computer coupled to the thermographic imaging system) via an input device to perform thermographic inspection. As another example, a user may control may program the thermographic inspection system (or the computer) to perform thermographic inspection. The thermographic inspection system may output a result that indicates whether a potential defect exists. As one example, the output may include a thermographic image that is displayed on a display device. Thus, the system may enable portable non-destructive testing of articles in the field.

In some implementations, the applique may be removed and reused on another test area of the article, on another article, or both. In a particular implementation, the applique may be removed without a solvent. By using an applique, the system may perform one-sided thermographic inspection techniques and may perform thermographic inspection on materials or surfaces with a high reflection coefficient (shiny or glossy surfaces, bare metal, white colored surfaces, etc.). Additionally, by utilizing removable appliques, the system may reduce surface preparation and cleaning time as compared to brush on or spray on paint and coatings. By reducing surface preparation and cleaning time, inspection times may are shortened and cost savings may be achieved. For example, material costs may be reduced as reusable appliques may replace (or reduce use of) paint, coatings, solvents, and cleaners. By using appliques with features that increase the amount of the light absorbed and an amount of the thermal radiation emitted, the appliques may produce higher quality test results than planar or colorized appliques.

FIG. 1 illustrates an example of a thermographic inspection system 100 that includes an applique 104, a testing light source 106, and a thermographic image capture device 108. The thermographic inspection system 100 enables non-destructive testing of an article 102. In some implementations, the thermographic inspection system 100 is portable. The thermographic inspection system 100 may generate a thermographic image (e.g., a thermogram) that indicates one or more potential defects in the article 102. The defects may be in the structure or the frame of the article 102, as described further with reference to FIG. 8. As illustrative, non-limiting examples, the defects may include disbonds, broken (e.g., cracked) structures or frames, surface cracks, and other structural flaws (e.g., sub-surface flaws). To illustrate, the thermographic image may indicate a disbond between an aluminum honeycomb core structure and an aluminum face sheet (e.g., an exterior surface) of a component of an aircraft, such as an airfoil of the aircraft. The aluminum honeycomb core structure may include an array of hollow hexagonal cells defined by a plurality of thin sidewalls. The aluminum honeycomb core structure may be position between two aluminum face sheets and may be bonded (e.g., adhesively bonded) to the two aluminum face sheets.

In a particular implementation of the thermographic inspection system 100, the article 102 may include or correspond to a component of an aircraft, a spacecraft, a rocket, a train, a ship, a submarine, a vehicle, a bridge, or a building, as illustrative, non-limiting examples. For example, the article 102 may be an airfoil or a fuselage of an aircraft. In some implementations, the article 102 may be a metallic (e.g., aluminum, titanium, etc.) article. For example, the article 102 may have a metallic surface, a metallic structure or frame, or both. In other implementations, the article 102 may be a non-metallic article (e.g., a composite material). For example, the article 102 may include a surface that is thermally conductive and non-metallic, a structure that is thermally conductive and non-metallic, or both. Additionally, the article 102 may have a high reflective coefficient, a low absorption coefficient, or both. For example, the article 102 may be efficient at reflecting electromagnetic radiation (e.g., the article 102 may have a high reflective coefficient) and inefficient at absorbing or emitting the electromagnetic radiation (e.g., the article 102 may have a low absorption coefficient), such that the article 102 reflects more electromagnetic radiation than the article 102 absorbs, emits, or both. In a particular implementation, the article 102 may have a high reflective coefficient and a low absorption coefficient for a portion of the electromagnetic spectrum. For example, the article 102 may reflect more light in the visible light spectrum than the article 102 absorbs, emits, or both. To illustrate, the article 102 may have a surface that has white colorization (e.g., a surface that reflects all visible light, or substantially all visible light), the article 102 may have a shiny or a glossy (e.g., reflective) finish, or both. In some implementations, the article 102 may include two or more surfaces, such as a first surface 112 and a second surface 114.

The applique 104 includes a first surface and a second surface and may be removably coupled to the article 102. For example, the first surface of the applique 104 may be affixed, adhered, or otherwise attached to a test area of the first surface 112 of the article 102 via surface tension (e.g., surface tension of intermolecular forces of molecules of the applique 104), static electricity (e.g., electrostatic adhesion or static cling), an adhesive material, an adhesive layer, or a combination thereof, as illustrative, non-limiting examples. The test area may correspond to an area (e.g., at least a portion) of the first surface 112 of the article 102. The area of the first surface 112 may be associated with a structure or frame of the article 102 that is coupled (e.g., bonded) to the first surface 112. The applique 104 may be removably coupled to (or decoupled from) the article 102 by applying pressure or a force to applique 104. In some implementations, the applique 104 may be affixed, adhered, or attached to the article 102 by a user. In other implementations, the applique 104 may be mechanically affixed, adhered, or attached to the article 102. For example, the applique 104 may be affixed, adhered, or attached to the article 102 by a thermographic inspection device, as described with reference to FIG. 7.

In some implementations, the applique 104 may be applied to the article 102 by utilizing vacuum pressure. In such implementations, the applique 104 may include a valve stem. For example, the valve stem may be coupled to the first surface of the applique 104 and may extend through the applique 104 or may be placed on the second surface of the applique 104 over a hole that extends through the applique 104. The valve stem be located in a corner of the applique 104 to reduce interference with thermographic imaging and provide a larger surface of the applique 104 to image. In some implementations, the valve stem may be a press fit valve stem or a threaded valve steam. The valve stem of the applique 104 may be coupled to a pump or a vacuum and may allow air that is located between the applique 104 and the article 102 to be removed. For example, the pump or vacuum may generate vacuum pressure which causes the air that is located between the applique 104 and the article 102 to be removed. Alternatively, the valve stem may be coupled to an airline via a 3-way valve (e.g., an aspirator) such that when the airline forces air (or water) through the 3-way valve vacuum pressure is generated between the applique 104 and the article 102 and the air is removed. By using vacuum pressure, air bubbles may be removed from between the applique 104 and the article 102 without manually working out air bubbles as the applique 104 is applied to the surface. In such implementations, the applique 104 may vinyl or rubber. In a particular implementations, the applique 104 may include a matte finish. By using a vacuum pressure to apply the applique 104, the applique may be re-used and the applique 104 may be applied to article 102 independent of adhesives.

In some implementations, a first portion of the applique 104 is removably coupled to the article 102, and a second portion of the applique 104 is not coupled (or is not removably coupled) to the article 102. For example, when the applique 104 is coupled to the article 102, there may be a gap between an edge or a corner of the applique 104 and the first surface 112. To illustrate, the edge or the corner of the applique 104 may not be affixed, adhered, or attached to the first surface 112 of the article 102. The edge or corner of the applique 104 may be used to remove the applique 104, as described with reference to FIG. 7. In a particular implementation, the edge or corner of the applique 104 includes a non-stick surface or coating, as an illustrative, non-limiting example. In another particular implementation, the edge or corner does not include an adhesive layer or an adhesive material, as an illustrative, non-limiting example.

At least a portion of the second surface of the applique 104 may oppose (e.g., may be opposite to) the first surface of the applique 104. For example, the applique 104 may be two sided, where a first side corresponds to the first surface of the applique 104 and a second side corresponds to the second surface of the applique 104. The second surface of the applique 104 may be configured to absorb electromagnetic radiation and to emit thermal energy based on the absorbed electromagnetic radiation. For example, the second surface of the applique 104 may receive and absorb light 122 from the testing light source 106. Additionally or alternatively, the applique 104 may absorb thermal energy by conduction or convection. As illustrative, non-limiting examples, heated fluid (or heated air) may be directed at the applique 104, the applique 104 may include a heat generation layer, or a heat generation device may be coupled to the applique 104.

The first surface of the applique 104 may be configured to transfer a first portion of the thermal energy by conduction to the article 102. For example, the first surface of the applique 104 may transfer (e.g., by conduction) heat 126 to the first surface 112 of the article 102. In some implementations, the head may also be transferred to the structure or frame of the article 102 that underlies the first surface 112. The second surface of the applique 104 may be configured to emit a second portion of the thermal energy as thermal radiation (e.g., infrared light or heat energy). For example, the second surface of the applique 104 may emit infrared light 124. The infrared light 124 may be captured by the thermographic image capture device 108, as further described herein. In some implementations, the applique 104 may be configured to substantially uniformly absorb the electromagnetic radiation, to substantially uniformly transfer the first portion of thermal energy to the article 102, and to substantially uniformly emit the second portion of the thermal energy as thermal radiation (e.g., the infrared light 124). As used herein substantially uniformly may include uniformly or near uniformly within a tolerance, such as a design tolerance, a fabrication or manufacturing tolerance, or measurement tolerance.

The substantially uniform transfer of thermal energy to the applique 104 and emission of thermal radiation may be disrupted by a defect in the article 102. A defect in the structure or frame of the article 102 may reduce the substantially uniform transfer of the thermal energy from the applique 104 to the article 102 and may result in a corresponding portion of the applique 104 transferring less thermal energy and emitting more thermal radiation than other portions of the applique 104. For example, in the example of a thermographic inspection system 100 illustrated in FIG. 1, a portion of the applique 104 that corresponds to (e.g., that is affected by or is above) a defect in the article 102 transfers less thermal energy (e.g., the heat 126) to the article 102 than surrounding areas of the applique 104 (e.g., areas that are not affect by the defect in the article 102). Accordingly, the portion of the applique 104 that corresponds to the defect in the article 102 emits more thermal radiation (e.g., the infrared light 124) than the surrounding areas of the applique 104. This difference in emission of thermal radiation may be captured by the thermographic image capture device 108 and may appear as a hot spot in a thermographic image. It is noted that an appearance of a hot spot in a thermographic image may depend on one or more image capture settings, such as a temperature range, scale, etc.

The applique 104 may be thermally conductive. For example, the applique 104 may more quickly transmit a portion of absorbed thermal energy (e.g., heat) to the article 102 by conduction, as compared to thermal insulators (e.g., rubber or air). To illustrate, the applique 104 may have one or more characteristics, such as a high thermal conductivity coefficient, may be thin, or a combination thereof, which enhance the ability of the applique 104 to conduct thermal energy. In some implementations, the applique 104 may include or may be formed from thermally conductive materials, such as materials having a high thermal conductivity coefficient. For example, one or more layers or surfaces of the applique 104 may include a thermally conductive material, such as vinyl, a polymer, a carbon fiber material, or a combination thereof.

In some implementations, the applique 104 may be thermally conductive in one direction. For example, the applique 104 may transfer the absorbed thermal energy in a first direction (e.g., from the applique 104 to the article 102) and may insulate transfer (e.g., diffusion) of thermal energy throughout (e.g., across) the applique 104. To illustrate, the applique 104 may include carbon nanotubes having a high degree of thermal conductivity in a first direction and a low degree of thermal conductivity in a second direction (e.g., among the carbon nanotubes). The carbon nanotubes may be oriented such that the thermal energy is conducted between the applique 104 and the article 102 instead of being diffused throughout the applique 104.

In some implementations, the applique 104 may include features configured to absorb electromagnetic radiation (e.g., the light 122) from the testing light source 106 and to emit thermal radiation (e.g., the infrared light 124). In a particular implementation, the features may be nanoscale features, such as features that may have dimensions ranging from 1 nanometer (nm) to 100 nm, as an illustrative, non-limiting example. In some implementations, the features may comprise a plurality of light absorbing cavities or a plurality of microstructures, as further described with reference to FIGS. 2-5. In some implementations, the light absorbing cavities may have a high aspect ratio, as described with reference to FIG. 3. The microstructures may include pyramids, cones, nanotubes, other shapes, or a combination thereof, as described with reference to FIGS. 4 and 5. Additionally, the features may be arranged in a pattern, such as a tessellated pattern or a rectangular pattern, as illustrative, non-limiting examples.

The applique 104 may be configured to absorb electromagnetic radiation produced by the testing light source 106. The testing light source 106 may include a light pulse device or a light flash device. The electromagnetic radiation produced by the testing light source 106 may have a high intensity, a short duration, or both. The electromagnetic radiation may be coherent or incoherent. As illustrative, non-limiting examples, the testing light source 106 may include an incandescent light source (regular or halogen), a fluorescent light source, one or more light emitting diodes (LEDs), a high intensity discharge lamp, a flashlamp, a flashtube (e.g., an electric arc), or a laser flash device.

In some implementations, the electromagnetic radiation (e.g., the light 122) produced by the testing light source 106 may include electromagnetic radiation from a particular portion of the electromagnetic spectrum. For example, the light 122 may include electromagnetic radiation from the visible light spectrum, the radio spectrum, the infrared spectrum, the ultraviolet spectrum, the microwave spectrum, the x-ray spectrum, the gamma ray spectrum, or a combination thereof. Additionally, the light 122 may include or correspond to electromagnetic radiation from a sub-portion of the electromagnetic spectrum. For example, the light 122 may include wavelengths associated with red light of the visible light spectrum or near infrared light of the infrared spectrum. In a particular implementation, the light 122 has multiple wavelengths including a first wavelength in the visible light spectrum and a second wavelength in the near infrared spectrum.

The testing light source 106 may be located proximate to the article 102 and the applique 104. The testing light source 106 may be configured to produce the electromagnetic radiation and to direct the electromagnetic radiation towards the applique 104. For example, the testing light source 106 may produce the light 122 and, and the testing light source 106 may direct the light 122 towards the second surface of the applique 104. To illustrate, the light 122 may be directed towards the second surface of the applique 104 at a first angle (e.g., an incident angle) with respect to the second surface of the applique 104. The first angle may be adjusted by a user or may be computer-controlled by making a physical adjustment to the testing light source 106, to the article 102, or both, as described with reference to FIG. 7. In some implementations, one or more properties of the electromagnetic radiation (e.g., the light 122) of the testing light source 106 may be adjusted. For example, a type of the electromagnetic radiation, an intensity of the electromagnetic radiation, a duration of the electromagnetic radiation, or the angle of incidence, of the electromagnetic radiation may be adjusted, as further described with reference to FIG. 7.

In some implementations, the applique 104 may include a heat generation layer. In such implementations, the testing light source 106 may or may not be used. To illustrate, the applique 104 may include a layer of indium tin oxide (ITO) located between the first surface of the applique 104 and the second surface of the applique 104. The layer of ITO may be configured to generate heat, as described with reference to FIG. 6, such that the testing light source 106 is omitted during the thermographic inspection process.

The applique 104 may be configured to emit thermal radiation that is captured by the thermographic image capture device 108. The thermographic image capture device 108 may be aligned with or placed on the applique 104. The thermographic image capture device 108 may include a thermographic camera or a thermographic inspection device, such as a temperature sensor device. The thermographic image capture device 108 may be a manual operated device or an automated device. For example, the thermographic image capture device 108 may be manually controlled by a user or may be remotely controlled by a computer, as described with reference to FIG. 7. The thermographic image capture device 108 may be configured to capture (or measure) the thermal radiation. For example, the thermographic image capture device 108 may capture the infrared light 124 emitted by the applique 104. In a particular implementation, the thermographic image capture device 108 captures (e.g., detects) the infrared light 124 having a wavelength in the near infrared spectrum. In other implementations, the thermographic image capture device 108 may capture (e.g., detect) infrared light having a wavelength in one or more of the infrared sub-spectrums (e.g., medium infrared, long infrared, etc.). The thermographic image capture device 108 may be configured to generate a thermographic image (e.g., a thermogram) based on the thermal radiation. The thermographic image may indicate a temperature gradient (e.g., a heat map, a heat distribution, etc.) of the applique 104. For example, the thermographic image may indicate the amount of thermal energy at different areas of the second surface of the applique 104. The thermographic image may indicate or include one or more hot spots (e.g., areas of increased temperature) or one or more cool spots that are indicative of a potential defect in the article 102.

In some implementations, the testing light source 106, the thermographic image capture device 108, or both, may be remotely controlled. For example, the testing light source 106, the thermographic image capture device 108, or both may be coupled, via a wired connection, a wireless connection or both, to an input device or a computer. Furthermore, the testing light source 106, the thermographic image capture device 108, or both, may be automated and computer-controllable, as described with reference to FIG. 7.

In some implementations, the thermographic inspection system 100 may include calibration and adjustment equipment, such as a spectral analyzer, a peel test device, a micrometer, an eddy current measurement device, or a combination thereof, as described with reference to FIG. 7. The calibration and adjustment equipment may be configured to adjust one or more components of the thermographic inspection system 100 and to produce thermographic images with a high signal to noise ratio. Additionally, the thermographic inspection system 100 may include a processor, a controller, one or more interfaces (e.g., a wired interface, a wireless interface, or both), or a combination thereof, as described with reference to FIG. 7.

During operation of the thermographic inspection system 100, the first surface of the applique 104 may be affixed (or adhered) to the test area of the article 102. For example, the first surface of the applique 104 may be affixed (or adhered) to the first surface 112 of the article 102 (e.g., a component of the vehicle 1102) by surface tension, static electricity, or both. To illustrate, molecules (e.g., polymer chains) of the applique 104 may be stretched when affixing (or adhering) the applique 104 to the first surface 112. The stretched molecules may attempt to return (e.g., recoil) to the molecules' un-stretched form or length, thereby creating surface tension that adheres the applique 104 to the first surface 112. Additionally or alternatively, the applique 104 may be configured to generate or conduct static electricity. For example, the applique 104 may develop a charge (e.g., positive or negative) that is opposite a charge of the first surface of the article 102. These opposite charges generate electrostatic adhesion between the applique 104 and the first surface 112. Additionally or alternatively, the first surface of the applique 104 may include an adhesive that enables the applique 104 to couple to the article. In some implementations, the applique 104 may include the valve stem and may be applied to the test area of the article 102 by vacuum pressure. For example, the applique 104 may be placed over the test area and coupled to a vacuum pump. The vacuum pump may be activated and may generate vacuum pressure which causes the air located between the applique 104 and the test area to be removed.

The testing light source 106 may be oriented towards the second surface of the applique 104. The testing light source 106 may produce and direct a light pulse or a light flash (e.g., the light 122) at the second surface of the applique 104. The second surface of the applique 104 may absorb a portion of the light 122 and may generate (or emit) thermal energy based on the absorbed portion of the light 122. The applique 104 may conduct a portion of the thermal energy from the second surface of the applique 104 to the first surface of the applique 104, and the first surface of the applique 104 may transfer a portion (e.g., the first portion) of the thermal energy to the article 102. For example, the first surface of the applique 104 may transfer the thermal energy by conducting the heat 126 to the article 102. The applique 104 may emit another portion (e.g., the second portion) of the thermal energy as the infrared light 124.

The thermographic image capture device 108 may capture the infrared light 124. The thermographic image capture device 108 may produce a thermographic image (e.g., thermographic data presented as the thermographic image) based on the captured infrared light 124. In a particular implementation, the thermographic image may be analyzed by a user. In another particular implementation, the thermographic image may be analyzed by a computer, as further described with reference to FIG. 7. The thermographic image may be analyzed to identify defects in the article 102.

If a defect is present in the article 102, a portion of the applique 104 that corresponds to (e.g., that is located above as illustrated in FIG. 1) the defect may transfer less thermal energy (e.g., the heat 126) to the article 102 than other portions of the applique 104. For example, the defect may impede transfer of the heat 126 causing a corresponding portion of the applique 104 to retain more thermal energy. Accordingly, the portion of the applique 104 that corresponds to the defect may emit more thermal energy as the infrared light 124 than other portions of the applique 104. Thus, a hot spot may be located in a thermographic image at a location corresponding to the defect in the article 102. In two-side thermographic inspection, the defect may be indicated by a cold spot in the thermographic image. For example, the defect may impede the heat 126 from transferring through the article 102 (e.g., from the second surface 114 to the first surface 112). Thus, a thermographic image generated by the thermographic image capture device 108 may be analyzed to identify hot spots (or cold spots) that indicate defects in the article 102. Additionally or alternatively, the thermographic image may be compared to one or more thermographic images generated during a previous thermographic imaging process, a diagram of the article 102, or both, to identify changes in thermal conductivity of the article 102. Changes in thermal conductivity may indicate formation of a defect in the article 102.

In some implementations, a thickness of the applique 104 may be considered during analysis of the thermographic image. For example, the thickness of the applique 104 may be measured before and after application to the article 102 to account for uneven application of the applique 104 or uneven surfaces of the test area of the article 102. To illustrate, a first thickness of the applique 104 may be measured by a micrometer before application of the applique 104 to the test area, and a second thickness of the applique 104 may be measure by an eddy current measuring device after application of the applique 104 to the test area. A difference between the first thickness and the second thickness may be used in during analysis of the thermographic image to identifying hot spots (or cool spots) in the thermographic image. For example, the thermographic image (or a portion thereof) may be adjusted based on the thickness. As an illustrative, non-limiting example, a processor may receive the thermographic image and the difference and may adjust (e.g., increase) temperatures for a portion of the thermographic image (e.g., thermographic image data) in response to determining the first thickness is less than the second thickness. As another example, one or more settings of a display device may be adjusted based on the difference.

After the thermographic inspection process is complete, the applique 104 may be removed from the article 102. In a particular implementation, the applique 104 may be removed independent of a solvent. To illustrate, the applique 104 may be removed without using a solvent, such as when the applique 104 is adhered to the article 102 using static electricity. In some implementations, after removal of the applique 104 subsequent to a first test, the applique 104 may be reused in a second test. For example, after removal of the applique 104 from the test area of the article 102, the applique 104 may be applied to a second test area of the article 102 or to another article and the thermographic inspection process may be repeated to generate another thermographic image.

In some implementations, if a potential defect is indicated by the thermographic image, a second thermographic inspection may be performed. The second thermographic inspection may use a different technique and different equipment than the thermographic inspection described with reference to FIG. 1. As part of the second thermographic inspection, a layer of paint or a coating may be applied to the test area of the article 102. The testing light source 106 may apply second light and the thermographic image capture device 108 may capture second infrared light. The thermographic image capture device 108 may generate a second thermographic image based on the second infrared light. The second thermographic image may be analyzed to confirm presence of a potential defect in the article 102. Because the second thermographic inspection is performed using different techniques and different equipment, the second thermographic inspection may have a different accuracy than the thermographic inspection performed by the thermographic inspection system 100.

In an alternate implementation, the applique 104 may be used in two-sided thermographic inspection processes. In this implementation, the testing light source 106 and the thermographic image capture device 108 may be directed at opposing surfaces, such as the first surface 112 of the article 102 and the second surface 114 of the article 102, respectively. To illustrate, the testing light source 106 may apply the light 122 to the applique 104 attached to the first surface 112 of the article 102. The thermographic image capture device 108 may capture infrared light from the second surface 114 of the article 102. Potential defects may be indicated by cool spots in a thermographic image based on the captured infrared light from the second surface 114. Additionally or alternatively, the applique 104 may be attached to the second surface 114 of the article 102. To illustrate, the applique 104 may be attached to the second surface 114 instead of the first surface 112 of the article 102, or a second applique may be attached to the second surface 114 in addition to the first applique 104 being attached to the first surface 112. In a particular implementation, the second applique may be different from the applique 104. For example, the second applique may include a heat generation layer as described with reference to FIG. 6.

Thus, the thermographic inspection system 100 may enable portable non-destructive testing of the article 102. The thermographic inspection system 100 may be configured to perform one-sided thermographic inspection techniques or two-sided thermographic inspection techniques. The thermographic inspection system 100 may perform thermographic inspection on materials with a high reflection coefficient, such as shiny glossy surfaces, bare metal surfaces, white colored surfaces, etc. By utilizing removable appliques, the thermographic inspection system 100 may reduce surface preparation and cleaning time as compared to brush on or spray on paint and coatings. By reducing surface preparation and cleaning time, inspection times may are shortened and cost savings may be achieved from reduced labor and material costs. For example, material costs may be reduced as reusable appliques may replace paint, coatings, solvents, and cleaners, or reduce an amount of paint, coatings, solvents, and cleaners.

Figure 2:
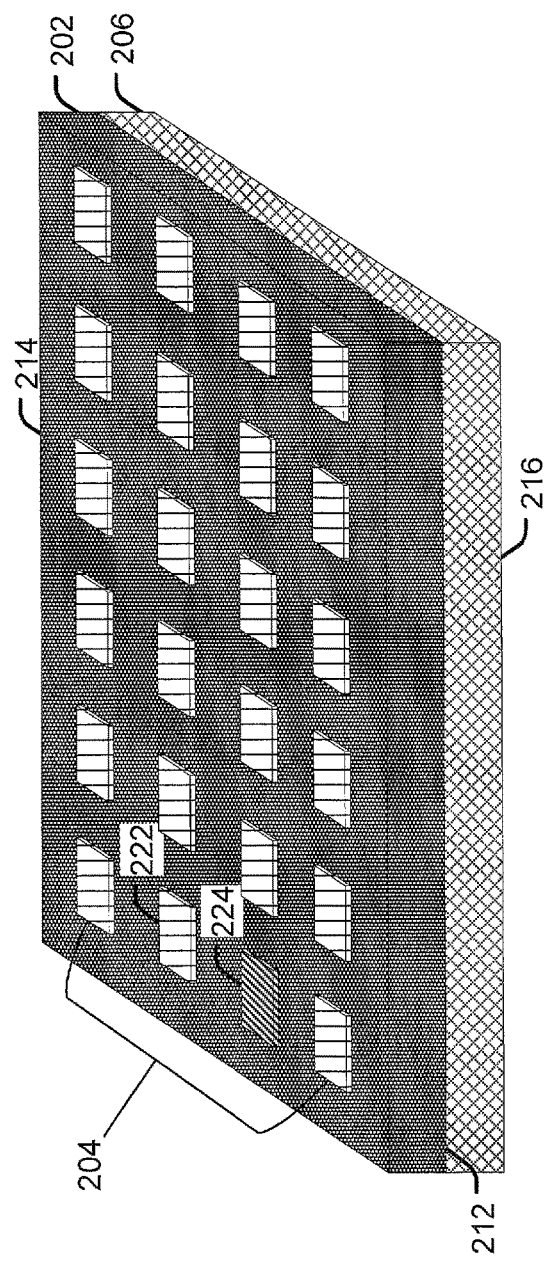
FIG. 2 is a diagram that illustrates an example of an applique for thermographic inspection.

FIG. 2 is a diagram that illustrates an example of an applique 200. The applique 200 may include or correspond to the applique 104 of FIG. 1. The applique 200 may be used for thermographic inspection of one or more articles, such as the article 102 of FIG. 1.

The applique 200 includes a thermally conductive layer 202 (e.g., a thermal transfer layer). In some implementations, the applique 200 may also include an adhesive layer 206, as described further herein. The thermally conductive layer 202 includes a first surface 212 and a second surface 214. The first surface 212 may be removably coupled to an article. The second surface 214 may include a plurality of features 204 and a portion of the second surface 214 may oppose the first surface 212. The first surface 212 and the second surface 214 may include or correspond to the first surface and the second surface of the applique 104 of FIG. 1, respectively. The first surface 212 may be configured to transfer (e.g., by conduction) thermal energy to the article, and the second surface 214 may be configured to absorb electromagnetic radiation (e.g., from a testing light source) and to emit thermal radiation, as described with reference to FIG. 1.

The plurality of features 204 may be configured to absorb radiation, such as electromagnetic radiation. For example, the plurality of features 204 may be formed of a material with a high absorption coefficient, may have a dark (e.g., black) colorization, may have a matte finish, may have a structure that increase a number of refractions (e.g., reflections) of incoming radiation to the applique 200, or a combination thereof. The plurality of features 204 may increase an amount of the radiation (e.g., electromagnetic radiation) that the applique absorbs, as compared to an applique with a planar or colorized surface. For example, the plurality of features may refract (e.g., reflect) and absorb incoming light multiple times, while a planar applique may refract (e.g., reflect) and absorb incoming light one time.

The plurality of features 204 may be arranged, formed, or disposed on the applique 200 in a pattern. For example, the plurality of features 204 may have a tessellated pattern, a rectangular pattern (e.g., aligned in rows and columns), or both. In other implementations, the plurality of features 204 may be arranged, formed, or disposed randomly on the applique 200. In some implementations, a first subset of the plurality of features 204 may be arranged, formed, or disposed on the applique 200 in a pattern while a second subset of the plurality of features 204 may be arranged, formed or disposed randomly on the applique 200. The plurality of features 204 may be adjacent to each other. For example, a tessellated pattern may not have a gap or spacing between features of the plurality of features. In other implementations, there may be a gap or spacing between one or more features of the plurality of features 204. For example, a tessellated pattern may include spaces between one or more features of the plurality of features 204. The spaces may form a three-dimensional lattice structure as depicted in FIG. 2.

The plurality of features 204 may include one or more cavities, microstructures, air vents, nanoparticles (e.g., quantum dots), or a combination thereof. As illustrative, non-limiting examples, the microstructures may include a groove, a cone, a pyramid, a tube, a cylinder, or a combination thereof. The plurality of features 204 may include a combination of different types of features. As an illustrative, non-limiting example, the plurality of features 204 may include one or more cavities, such as a representative cavity 222, and one or more microstructures, such as a representative microstructure 224. In a particular implementation, the one or more microstructures may include multiple microstructures that include different types of microstructures, as described with reference to FIGS. 4 and 5. For example, the one or more microstructures may include a first microstructure that includes a pyramid and a second microstructures that includes a nanotube. Additionally or alternatively, the one or more cavities may include multiple cavities that have different sizes, different shapes, different depths, or a combination thereof, as described with reference to FIG. 3. In a particular implementation, the second surface 214, the plurality of features 204, or both, may be include a layer of nanoparticles. To illustrate, quantum dots (nano-size particles) may be deposited on the second surface 214, the plurality of features 204, or both. The quantum dots may increase absorptivity (e.g., an absorption coefficient) of radiation in the visible light spectrum.

In some implementations, the adhesive layer 206 may be coupled to or in contact with the thermally conductive layer 202. The adhesive layer 206 may be located or positioned between the thermally conductive layer 202 and the article (e.g., a test area of the article). For example, the adhesive layer 206 may include a third surface 216 that is coupled to the article 102. In such implementations, the second surface 214 of the thermally conductive layer may be coupled to or in contact with another surface of the adhesive layer 206 (e.g., the second surface 214 may not be directly coupled to the article). In these implementations, the third surface 216 may include or correspond to the first surface of the applique 104 of FIG. 1.

The adhesive layer 206 may be configured to removably couple the applique 200 to the article. For example, the applique 200 may be attachable to the article. The adhesive layer 206 may include or correspond to an elastic film, an adhesive material or chemical, an electrically conductive or generating material (e.g., static electricity conductive), or a combination thereof. The adhesive layer 206 may be configured to generate surface tension (e.g., intermolecular surface tension), generate electrostatic adhesion, generate mechanical adhesion (e.g., adhesive bonds, velcro, etc.), or a combination thereof. In a particular implementation, the adhesive layer 206 may be an adhesive material that is applied to the first surface 212 of the thermally conductive layer 202 or to the test area of the article.

In some implementations, the adhesive layer 206 may be thermally conductive. For example, the adhesive layer 206 may include thermally conductive materials or components. For example, the adhesive layer may include thermally conductive polymers or thermally conductive nanotubes. In some implementations, the adhesive layer 206 may be thermally conductive in one direction. For example, the applique 200 may act as a thermally conductor in a first direction (e.g., from the applique 200 to the article) and may act as a thermal insulator in a second direction (e.g., across the applique 200). To illustrate, the applique 200 may transfer twice as much thermal energy in the first direction as compared to thermal energy that is diffused throughout the applique 200.

By including the plurality of features 204 in the applique 200, the applique 200 may have increased thermal emissivity as compared to appliques with planar surfaces or colorized surfaces, to paint or coatings, or both. By increasing thermal emissivity of the applique 200, higher quality thermographic images may be generated during thermographic inspection. For example, a thermographic image generated using the applique 200 may have a higher signal to noise ratio than a thermographic image generated using an applique with planar or colorized surfaces. As another example, a thermographic image generated using the applique 200 may have a higher signal to noise ratio than a thermographic image generated using paint or coatings (e.g., flat black paint or lampblack coatings).

Figure 3:
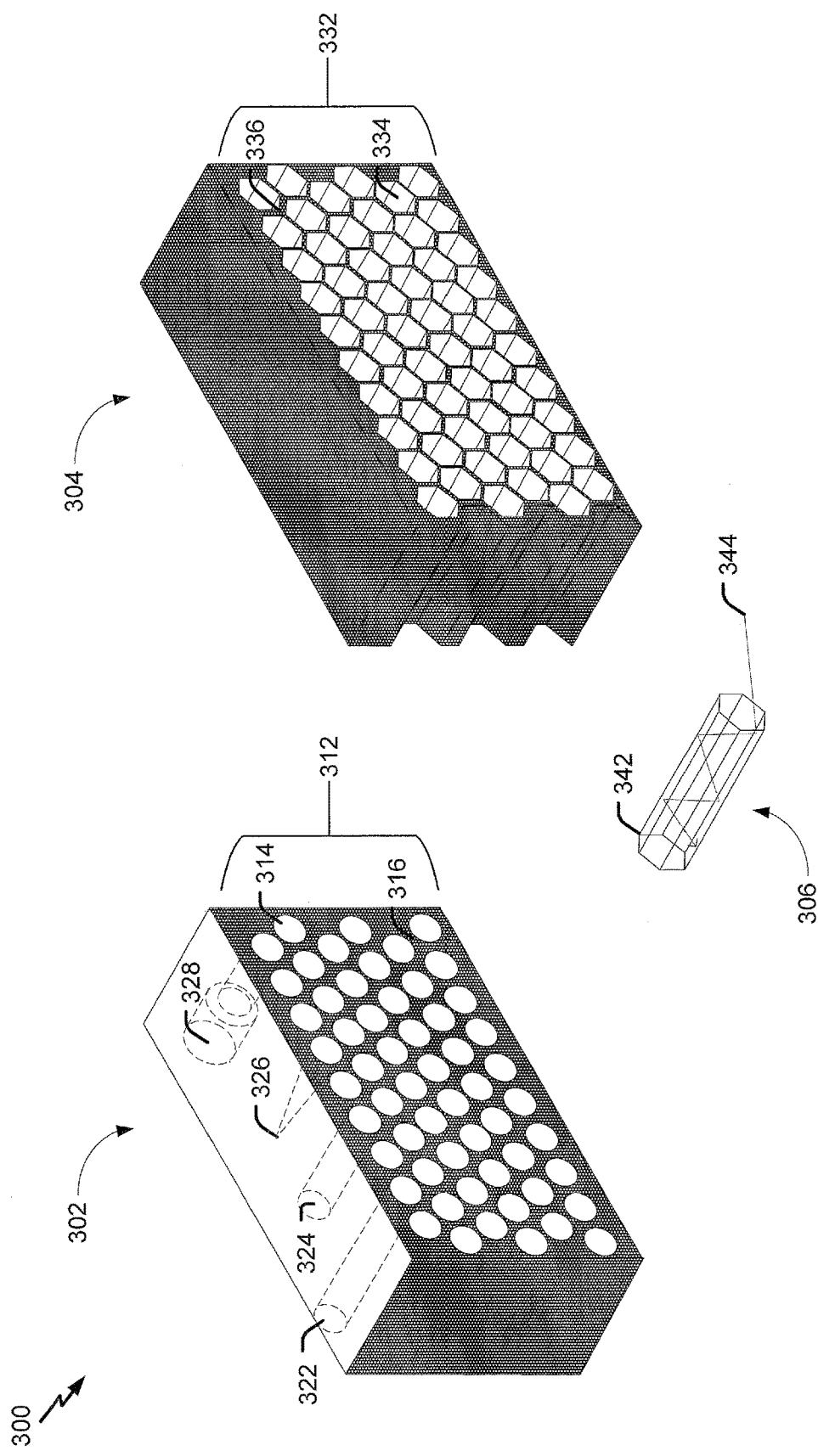
FIG. 3 is a diagram that illustrates a particular example of an applique for thermographic inspection that includes a plurality of cavities.

FIG. 3 is a diagram 300 that illustrates examples of appliques 302, 304. Each of the appliques 302, 304 includes a plurality of cavities. Each of the applique 302 and the applique 304 may include or correspond to the applique 104 of FIG. 1, the applique 200 of FIG. 2, or both. The appliques 302, 304 may be used for thermographic inspection of one or more articles, such as the article 102 of FIG. 1.

The applique 302 includes a thermally conductive layer and a plurality of light absorbing cavities 312 having a circular cross-section 314 (e.g., an aperture). The thermally conductive layer includes a first surface and a second surface. The first surface may be removably coupled to an article. The second surface may include the plurality of light absorbing cavities 312 and a portion of the second surface may oppose the first surface. The first surface and the second surface may include or correspond to the first surface and the second surface of the applique 104 of FIG. 1, respectively. The first surface may be configured to transfer (e.g., by conduction) thermal energy to the article, and the second surface may be configured to absorb electromagnetic radiation (e.g., from a testing light source) and to emit thermal radiation, as described with reference to FIG. 1. In a particular implementation, the second surface may have a light absorption coefficient and a light reflection coefficient, and the light absorption coefficient may be greater than the light reflection coefficient.

The plurality of light absorbing cavities 312 may be arranged, formed, or disposed on the applique 302 randomly or in a pattern. For example, the plurality of light absorbing cavities 312 may have a tessellated pattern, a rectangular pattern (e.g., aligned in rows and columns), a diagonal pattern, or a combination thereof. In some implementations, plurality of light absorbing cavities 312 may be adjacent to each other. For example, a tessellated pattern may not have a gap or spacing between cavities of plurality of light absorbing cavities 312. In other implementations, there may be a gap or spacing between one or more cavities of the plurality of light absorbing cavities 312. For example, a tessellated pattern may include spaces between one or more cavities of the plurality of light absorbing cavities 312. The spaces may form a three-dimensional (3D) lattice structure 316 (e.g., a web-shaped structure), as illustrated in FIG. 3.

In some implementations, one or more of the plurality of light absorbing cavities 312 may extend through the thermally conductive layer from the first surface to the second surface of the applique 302 (e.g., a cavity 322). To illustrate, the first surface and the second surface may define the plurality of light absorbing cavities 312, and the portion of the second surface (e.g., the 3D lattice structure 316) may oppose a portion of the first surface. The cavity 322 may act as an air vent and may allow air between the applique 302 and the article to escape (e.g., vent) during application of the applique 302 to the article.

In some implementations, one or more of the plurality of light absorbing cavities 312 may partially extend through the thermally conductive layer of the applique 302 (e.g., a cavity 324). To illustrate, the second surface may define the plurality of light absorbing cavities 312, and the portion of the second surface (e.g., the 3D lattice structure 316) may oppose the first surface.

In some implementations, one or more of the plurality of light absorbing cavities 312 may have a different or varying cross-section as the cavity extends through the thermally conductive layer of the applique 302 (e.g., a cavity 326 or a cavity 328). In a particular example, a cavity (e.g., the cavity 326) may have a smaller cross-section than the circular cross-section 314 at the second surface. For example, as illustrated in FIG. 3, the cavity 326 has the circular cross-section 314 at the second surface and has a different shaped cross-section at an opposite end (e.g., an end nearest the first surface). The cavity 326 may be tapered and have a cone-like shape (e.g., a funnel-like shape). Although FIG. 3 illustrated the cavity 326 extending partially though the applique 302, in other implementations, the cavity 326 may extend through the applique 302 to the first surface. In another particular example, a cavity (e.g., the cavity 328) may have a larger cross-section than the circular cross-section 314 at the second surface. For example, as illustrated in FIG. 3, the cavity 328 has a larger circular cross-section at the opposite end (e.g., the end nearest the first surface) than the circular cross-section 314 at the second surface. In some implementations, the cavity 328 may include or correspond to a blackbody cavity.

Referring to the applique 304, the applique 304 includes a thermally conductive layer and a plurality of light absorbing cavities 332 having a hexagonal cross-section 334 (or aperture). Although illustrated as having the hexagonal cross-section 334, in other implementations, the cross-section may be another shape, such as another polygon shaped cross-section. The thermally conductive layer includes a first surface and a second surface. The first surface may be removably coupled to the article. The second surface may include light absorbing cavities 332 and a portion of the second surface may oppose the first surface. The first surface and the second surface may include or correspond to the first surface and the second surface of the applique 104 of FIG. 1, respectively. The first surface may be configured to transfer (e.g., by conduction) thermal energy to the article, and the second surface may be configured to absorb electromagnetic radiation (e.g., from a testing light source) and to emit thermal radiation, as described with reference to FIG. 1.

In some implementations, one or more of the light absorbing cavities 332 of the applique 304 may be arranged in a pattern, may extend through the thermally conductive layer to the first surface of the applique 304 (e.g., the cavity 322), may partially extend through the thermally conductive layer of the applique 304 (e.g., the cavity 324), may have a different or varying cross-sections as the cavity extends through the thermally conductive layer of the applique 304 (e.g., the cavity 326 or the cavity 328), or a combination thereof, as described with reference to the applique 302.

In some implementations, the appliques 302, 304 may include an adhesive layer, such as the adhesive layer 206 of FIG. 2. The adhesive layer may be coupled to or in contact with the appliques 302 and 304 and may be located or positioned between the appliques 302 and 304 and an article (e.g., a test area of the article).

In other implementations, the appliques 302, 304 may have light absorbing cavities with different shapes. For example, the appliques 302, 304 may have a rectangular (e.g., a slit) cross-section, a triangular cross-section, a pentagonal cross-section, an octagonal cross-section, etc.

During a thermographic inspection process, light may be applied from a testing light source, such as the light 122 from the testing light source 106 of FIG. 1. The plurality of light absorbing cavities 312 and 332 (of the appliques 302, 304) may absorb the light. For example, diagram 306 illustrates a particular light absorbing cavity 342 with a hexagonal cross-section. A ray of light 344 of the light from the testing light source may enter a representative cavity 342 of one of the appliques 302, 304 and may be refracted (e.g., reflected) along interior sidewalls of the cavity 342. A portion of the ray of light 344 may be absorbed by the cavity 342 each time the ray of light 344 is refracted along the interior sidewalls. The greater an aspect ratio (e.g., a ratio of a depth of a cavity to a diameter of a cross-section of the cavity) the cavity 342, the more refractions and energy is absorbed from the ray of light 344. Accordingly, the more energy that is absorbed increases the thermal radiation able to be emitted by the appliques 302, 304.

By including the plurality of light absorbing cavities in the appliques 302, 304, the appliques 302, 304 may have increased thermal absorption and emissivity as compared to appliques with planar surfaces or colorized surfaces, to paint or coatings, or both. By increasing the thermal emissivity of the appliques 302, 304, higher quality thermographic images may be generated during thermographic inspection. For example, a thermographic image generated using the appliques 302, 304 may have a higher signal to noise ratio than a thermographic image generated using an applique with planar or colorized surfaces. As another example, a thermographic image generated using the appliques 302, 304 may have a higher signal to noise ratio than a thermographic image generated using paint or coatings (e.g., flat black paint or lampblack coatings).

Figure 4:
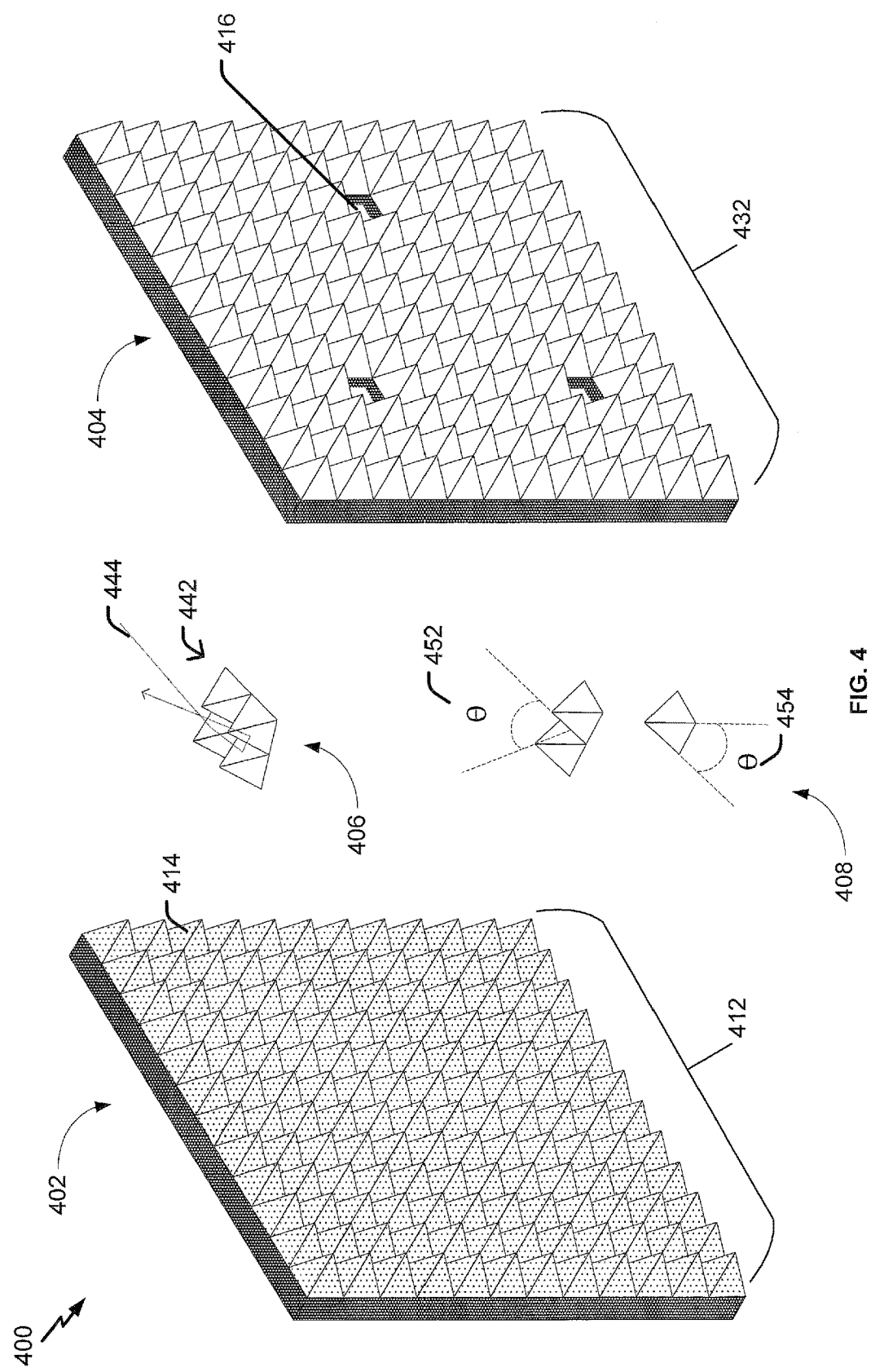
FIG. 4 is a diagram that illustrates a particular example of an applique for thermographic inspection that includes a plurality of microstructures.

FIG. 4 is a diagram 400 that illustrates examples of appliques 402, 404 that each include a plurality of microstructures. Each of the applique 402 and the applique 404 may include or correspond to the applique 104 of FIG. 1, the applique 200 of FIG. 2, the appliques 303, 304 of FIG. 3, or a combination thereof. The appliques 402, 404 may be used for thermographic inspection of articles, such as the article 102 of FIG. 1.

The applique 402 includes a thermally conductive layer and a plurality of microstructures 412. The thermally conductive layer includes a first surface and a second surface. The first surface may be removably coupled to the article. The second surface may include the plurality of microstructures 412 and the second surface may oppose the first surface (e.g., the first surface and the second surface may be on opposite sides of the applique 402). To illustrate, the plurality of microstructures 412 may extend (or protrude) from the second surface. The first surface and the second surface may include or correspond to the first surface and the second surface of the applique 104 of FIG. 1, respectively. The first surface may be configured to transfer (e.g., by conduction) thermal energy to the article, and the second surface may be configured to absorb electromagnetic radiation (e.g., from a testing light source) and to emit thermal radiation, as described with reference to FIG. 1. In a particular implementation, a light absorption coefficient associated with the second surface may be greater than a light reflection coefficient associated with the second surface.

The plurality of microstructures 412 may be configured to absorb electromagnetic radiation. For example, the plurality of microstructures 412 may be formed of a material with a high absorption coefficient, the plurality of microstructures 412 may have a black colorization, the plurality of microstructures 412 may have a matte finish, the plurality of microstructures 412 may have a structure that increases a number of refractions (or reflections) of incoming electromagnetic radiation by the applique 402, or a combination thereof. In other implementations, the plurality of microstructures 412 may be substantially transparent, as described with reference to the applique 404. The plurality of microstructures 412 may include one or more grooves, cones, pyramids, tubes, cylinders, or a combination thereof. As used herein substantially transparent may include transparent or near transparent (e.g., translucent) within a tolerance, such as a design tolerance, a fabrication or manufacturing tolerance, or measurement tolerance.

The plurality of microstructures 412 may be configured to direct incoming electromagnetic radiation among the plurality of microstructures 412. For example, a particular microstructure of the plurality of microstructures 412 may be configured to refract (or reflect) incoming electromagnetic radiation among adjacent microstructures of the plurality of microstructures 412. Because the plurality of microstructures 412 increases a number of times incoming electromagnetic radiation is refracted among the plurality of microstructures 412 as compared to other materials that do not refract incoming electromagnetic radiation to adjacent areas, the applique 402 may absorb more of the incoming electromagnetic radiation than other materials. For example, the plurality of microstructures 412 and the second surface of the applique 402 may absorb a portion of the thermal energy of the incoming electrometric radiation each time the electromagnetic radiation is refracted to one or more of the plurality of microstructures 412 and the second surface. Accordingly, a cumulative amount of thermal energy absorbed by the applique 402 is increased with each additional refraction, and thus the applique 402 absorbs more thermal energy than other materials (e.g., materials that do not refract incoming electromagnetic radiation to adjacent areas).

To illustrate, referring to diagram 406 of FIG. 4, a ray of light 444 of the light from the testing light source may refract among multiple microstructures 442 of the plurality of microstructures 412. A portion of the ray of light 444 may be absorbed by each of the multiple microstructures 442 of the plurality of microstructures 412 each time the ray of light 444 is refracted by one of the multiple microstructures 442. An average number of refractions of the light by the plurality of microstructures 412 may be dependent on angles of the plurality of microstructures 412. Diagram 408 illustrates a first angle 452 between faces of two adjacent microstructures of the plurality of microstructures 412, and a second angle 454 between adjacent edges of a face of a microstructure (illustrated as a pyramid in FIG. 4). In a particular implementation, the first angle 452 and the second angle 454 are the same (e.g., 60 degrees). Designing the plurality of microstructures 412 such that the first angle 452, the second angle 454, or both, are increased may increase a number of refractions of light by the plurality of microstructures 412.

The plurality of microstructures 412 may be arranged, formed, or disposed on the applique 402 in a pattern. For example, the plurality of microstructures 412 may have a tessellated pattern, a rectangular pattern (e.g., microstructures may be aligned in rows and columns), a diagonal pattern, or a combination thereof. In some implementations, the plurality of microstructures 412 may be adjacent to each other. For example, a tessellated pattern may not have a gap or spacing between microstructures of plurality of microstructures 412 (e.g., a portion of a face of a microstructure may be in contact with at least a portion of a face of an adjacent microstructure), as illustrated in FIG. 4. In other implementations, there may be a gap or spacing between one or more microstructures of the plurality of microstructures 412. For example, a tessellated pattern may include spaces between one or more microstructures of the plurality of microstructures 412.

Referring to the applique 404, the applique 404 includes a thermally conductive layer and a plurality of microstructures 432. The thermally conductive layer includes a first surface and a second surface. The first surface may be removably coupled to the article. The second surface may include the plurality of microstructures 432 and a portion of the second surface may oppose the first surface (e.g., the first surface and the second surface may be on opposite sides of the applique 404). To illustrate, the plurality of microstructures 432 may extend (or protrude) from the second surface. The first surface and the second surface may include or correspond to the first surface and the second surface of the applique 104 of FIG. 1, respectively. The first surface may be configured to transfer (e.g., by conduction) thermal energy to the article, and the second surface may be configured to absorb electromagnetic radiation (e.g., from a testing light source) and to emit thermal radiation, as described with reference to FIG. 1.

In some implementations, the plurality of microstructures 432 may be arranged in a pattern as described with reference to the applique 402. The plurality of microstructures 432 may include one or more grooves, cones, pyramids, tubes, cylinders, or a combination thereof. Additionally, one or more of the plurality of microstructures 432 may be substantially transparent. For example, one or more of the plurality of microstructures 432 may be transparent or translucent (e.g., non-opaque). To illustrate, one or more of the plurality of microstructures 432 may absorb and scatter a small amount of electromagnetic radiation (e.g., have a low absorption coefficient and a low scattering coefficient) such that the second surface may be seen through the plurality of microstructures 432. As an illustrative, non-limiting example, the plurality of microstructures 432 may allow a portion (e.g., most) of incoming electromagnetic radiation having wavelengths in the visible light spectrum to pass through the plurality of microstructures 432. In a particular implementation, the plurality of microstructures 432 may include substantially transparent rectangular pyramids, as illustrated in FIG. 4. The plurality of microstructures 432 may be configured to direct (e.g., refract or focus) the electromagnetic radiation towards the second surface of the applique 404, where the electromagnetic radiation may be absorbed by the applique 404.

In some implementations, the applique 404 may include one or more air vents 416, as illustrated in FIG. 4. The one or more air vents 416 may be configured to allow air to escape (e.g., vent) from between the applique 404 and the article. The one or more air vents 416 may be defined by the first surface and the second surface of the applique 404. In some implementations, the one or more air vents 416 may be dispersed among the plurality of microstructures 432. For example, each of the one or more air vents 416 may be interspersed between multiple microstructures of the plurality of microstructures 432. In some implementations, the one or more air vents 416 may be dispersed among the plurality of microstructures 432 in a pattern. For example, every 100th or every 1000th microstructure of the plurality of microstructures 432 may be replaced with an air vent. In a particular implementation, the one or more air vents 416 may include or correspond to light absorbing cavities, such as the light absorbing cavities of FIG. 3. In a particular implementation, the applique 402 includes one or more air vents dispersed among the plurality of microstructures 412.

Because the appliques 402, 404 include the plurality of microstructures 412, 432, respectively, the appliques 402, 404 may have increased thermal absorption and emissivity as compared to appliques with planar surfaces or colorized surfaces or to articles that are painted or covered in a coating. Because of the thermal emissivity of the appliques 402, 404, higher quality thermographic images may be generated during thermographic inspection of the appliques 402, 404 than during inspection of other appliques. For example, a thermographic image generated using the appliques 402, 404 may have a higher signal to noise ratio than a thermographic image generated from an applique with planar or colorized surfaces. As another example, a thermographic image generated using the appliques 402, 404 may have a higher signal to noise ratio than a thermographic image generated from a painted article (e.g., using flat black paint) or an article having a coating (e.g., a lampblack coating).

Figure 5:
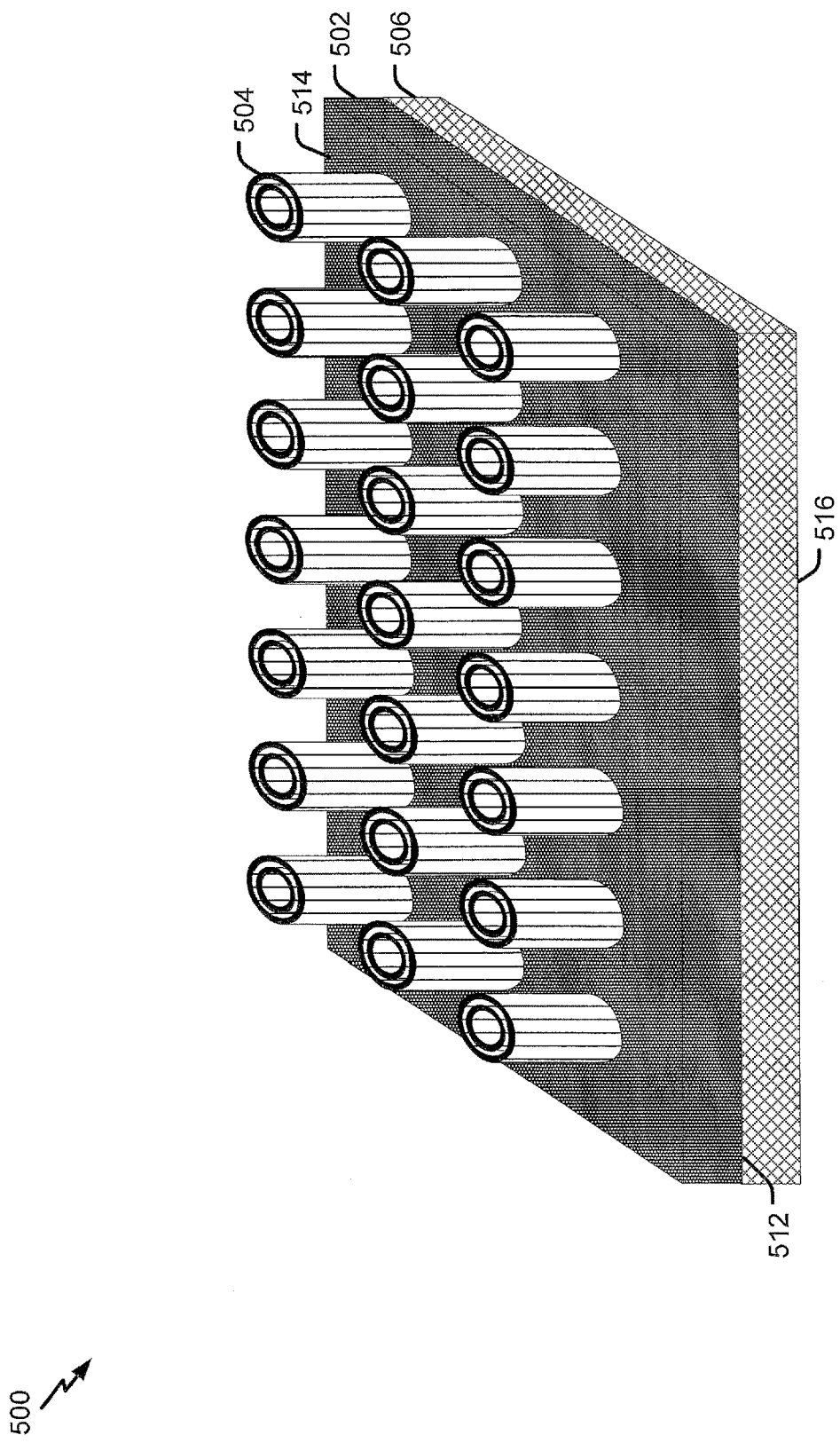
FIG. 5 is a diagram that illustrates a particular example of an applique for thermographic inspection that includes a plurality of nanotubes.

FIG. 5 illustrates is a diagram that illustrates a particular example of an applique 500 that includes a plurality of nanotubes. The applique 500 may include or correspond to the applique 104 of FIG. 1, the applique 200 of FIG. 2, the appliques 302, 304 of FIG. 3, the appliques 402, 404 of FIG. 4, or a combination thereof. The applique 500 may be used during thermographic inspection of one or more articles, such as the article 102 of FIG. 1.

The applique 500 includes a thermally conductive layer 502 and a plurality of nanotubes 504. The thermally conductive layer 502 includes a first surface 512 and a second surface 514. The first surface 512 may be removably coupled to an article. The second surface 514 may include the plurality of nanotubes 504 and a portion of the second surface 514 may oppose the first surface 512 (e.g., the first surface 512 and the second surface 514 may be on opposite sides of the applique 500). To illustrate, the plurality of nanotubes 504 may extend (or protrude) from the second surface 514. The first surface 512 and the second surface 514 may include or correspond to the first surface and the second surface of the applique 104 of FIG. 1, respectively. The first surface 512 may be configured to transfer (e.g., by conduction) thermal energy received by the applique 500 to the article, and the second surface 514 may be configured to absorb electromagnetic radiation (e.g., light from a testing light source) and to emit thermal radiation, as described with reference to FIG. 1.

The plurality of nanotubes 504 may be configured to collect and absorb electromagnetic radiation (e.g., light). The plurality of nanotubes 504 may include a material having a high absorption coefficient, such as a carbon based material. The plurality of nanotubes 504 may absorb incoming light. For example, light may enter tubes of the plurality of nanotubes 504 and become trapped. To illustrate, incoming light may enter a particular tube of the plurality of nanotubes 504 and may be refracted (or reflected) on sidewalls of the particular tube multiple times. Each time the incoming light is refracted on a sidewall of the particular nanotube, a portion of the light is absorbed by the particular tube. Because the applique 500 includes multiple nanotubes (e.g., the plurality of nanotubes 504), incoming light may be refracted within nanotubes multiple times (e.g., more than once), as compared to appliques with planar surfaces that may only refract light a single time. Accordingly, the applique 500 may absorb more electromagnetic radiation and may emit more thermal radiation (due to the additional refraction and absorption provided by the plurality of nanotubes 504) than appliques with planar surfaces.

The plurality of nanotubes 504 may include single-walled nanotubes, multi-walled nanotubes, or a combination thereof. In a particular implementation, the plurality of nanotubes 504 may include carbon nanotubes. The plurality of nanotubes 504 may be arranged, formed, or disposed on the applique 500 in a pattern, as described with reference to FIGS. 2-4. In some implementations, the applique 500 may further include air vents, as described with reference to FIGS. 2-4.

In some implementations, the applique 500 may include an adhesive layer 506 that may be coupled to or may be in contact with the thermally conductive layer 502. The adhesive layer 506 may be located or positioned between the thermally conductive layer 502 and the article (e.g., a test area of the article). For example, the adhesive layer 506 may include a third surface 516 that is coupled to the article. In such implementations, the first surface 512 of the thermally conductive layer 502 may be coupled to or in contact with a surface of the adhesive layer 506 (e.g., the first surface 512 is not directly coupled to the article). In these implementations, the third surface 516 of the adhesive layer 506 may include or correspond to the first surface of the applique 104 of FIG. 1. The adhesive layer 506 may be configured to removably couple the applique 500 to the article, as described with reference to FIG. 2. The adhesive layer 506 may include or correspond to the adhesive layer 206 of FIG. 2.

Because the applique 500 includes the plurality of nanotubes 504, the applique 500 may have increased thermal absorption and emissivity as compared to appliques with planar surfaces or colorized surfaces and to articles that are painted or coated with a coating. Due to the thermal emissivity of the applique 500, higher quality thermographic images may be generated during thermographic inspection of the applique 500 that during thermographic images of other appliques or articles. For example, a thermographic image generated using the applique 500 may have a higher signal to noise ratio than a thermographic image generated using an applique with planar or colorized surfaces. As another example, a thermographic image generated using the applique 500 may have a higher signal to noise ratio than a thermographic image generated using an article that is painted (e.g., using a flat black paint) or covered with a coating (e.g., a lampblack coating).

Figure 6:
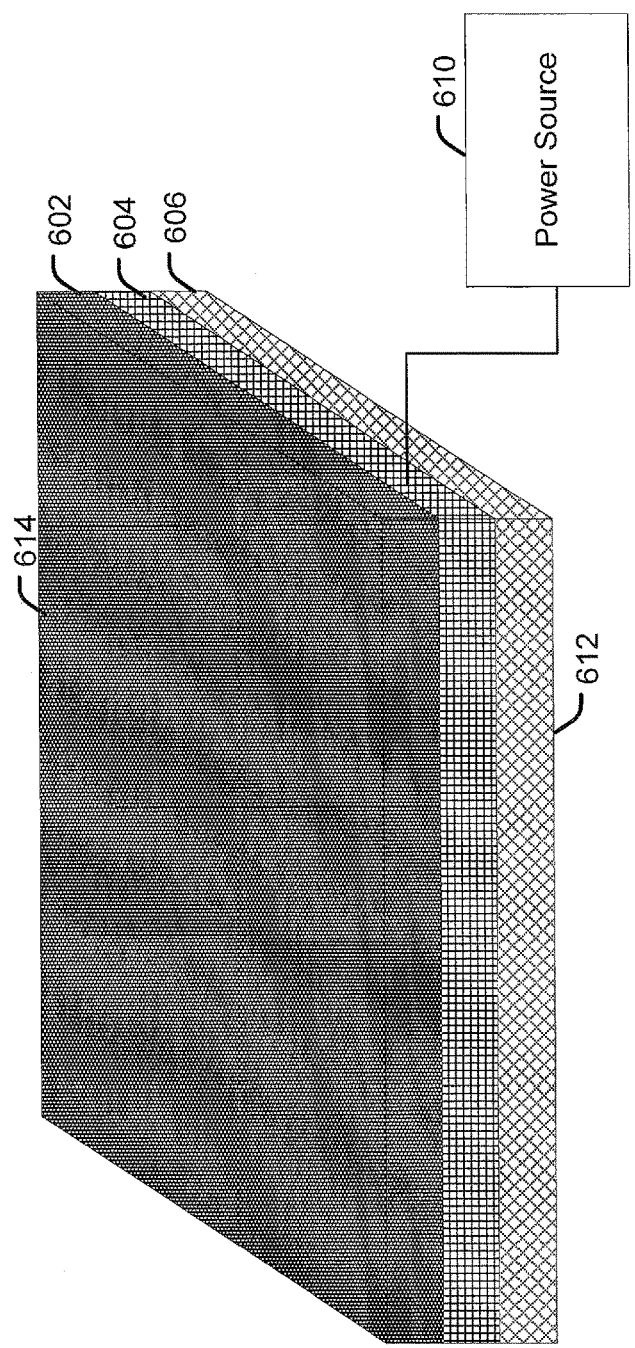
FIG. 6 is a diagram that illustrates a particular example of an applique for thermographic inspection that includes a heat generation layer.

FIG. 6 is a diagram that illustrates a particular example of an applique 600 that includes a heat generation layer. The applique 600 may include or correspond to the applique 104 of FIG. 1, the applique 200 of FIG. 2, the appliques 302, 304 of FIG. 3, the appliques 402, 404 of FIG. 4, the applique 500 of FIG. 5, or a combination thereof. The applique 600 may be used for thermographic inspection of one or more articles, such as the article 102 of FIG. 1.

The applique 600 includes a thermally conductive layer 602, a heat generation layer 604, and an adhesive layer 606. The heat generation layer 604 may be positioned between the thermally conductive layer 602 and the adhesive layer 606. The applique 600 includes a first surface 612 and a second surface 614. The first surface 612 may be removably coupled to an article. In some implementations, the second surface 614 may include a plurality of features and a portion of the second surface 614 may oppose the first surface 612, as described with reference to FIG. 2. In some implementations, the plurality of features may be arranged, formed, or disposed on the applique 600 in a pattern, as described with reference to FIG. 2. The plurality of features may include, cavities, microstructures, air vents, nanoparticles, or a combination thereof, as described with reference to FIGS. 2-5. The first surface 612 and the second surface 614 may include or correspond to the first surface and the second surface of the applique 104 of FIG. 1, respectively. The adhesive layer 606 may couple the applique 600 to the article and may include or correspond to the adhesive layer 206 of FIG. 2.

The heat generation layer 604 may be coupled to a power source 610 and may be configured to generate thermal energy (e.g. heat). For example, the power source 610 may apply a voltage and that generates a voltage difference (e.g., a voltage potential) across the heat generation layer 604. Due to the voltage difference, the heat generation layer 604 may generate thermal energy. Thus, the applique 600 may be used for a thermographic inspection that does not include a testing light source. As an illustrative, non-limiting example, the applique 600 may include a layer of indium tin oxide that is configured to generate the thermal energy. The thermal energy generated by the heat generation layer 604 may be transferred (e.g., by conduction) to the thermally conductive layer 602 and to the adhesive layer 606. The first surface 612 may be configured to transfer (e.g., by conduction) a first portion of the thermal energy to the article, and the second surface 614 may be configured to emit thermal radiation corresponding to a second portion of the thermal energy.

In other implementations, the applique 600 may include more layers or fewer layers than illustrated in FIG. 6. For example, the applique 600 may include a second thermally conductive layer positioned between the heat generation layer 604 and the adhesive layer 606. As another example, the applique 600 does not include the adhesive layer 606. In such implementations, the applique 600 includes the second thermally conductive layer positioned between the heat generation layer 604 and the article.

During operation, the applique 600 may be removably coupled to the article via the adhesive layer 606. The heat generation layer 604 of the applique 600 may be coupled to the power source 610 and the heat generation layer 604 may generate the thermal energy. The heat generation layer 604 may transfer the first portion of the thermal energy to the article via the adhesive layer 606. The heat generation layer 604 may transfer a second portion of the thermal energy to the thermally conductive layer 602. The second surface 614 of the applique 600 may emit the thermal radiation (e.g., infrared light) corresponding to at least a portion of the second portion of the thermal energy. A thermographic image capture device may receive the thermal radiation (e.g., the infrared light) and may generate a thermographic image based on the captured thermal radiation. The thermographic image may indicate potential defects, as described with reference to FIG. 1.

Because the applique 600 includes the heat generation layer 604, a thermographic inspection system may perform thermographic inspection on an article independent of a testing light source. Accordingly, the applique 600 may enable thermographic inspection to occur in environments where ambient light interferes with testing light sources.

Figure 7:
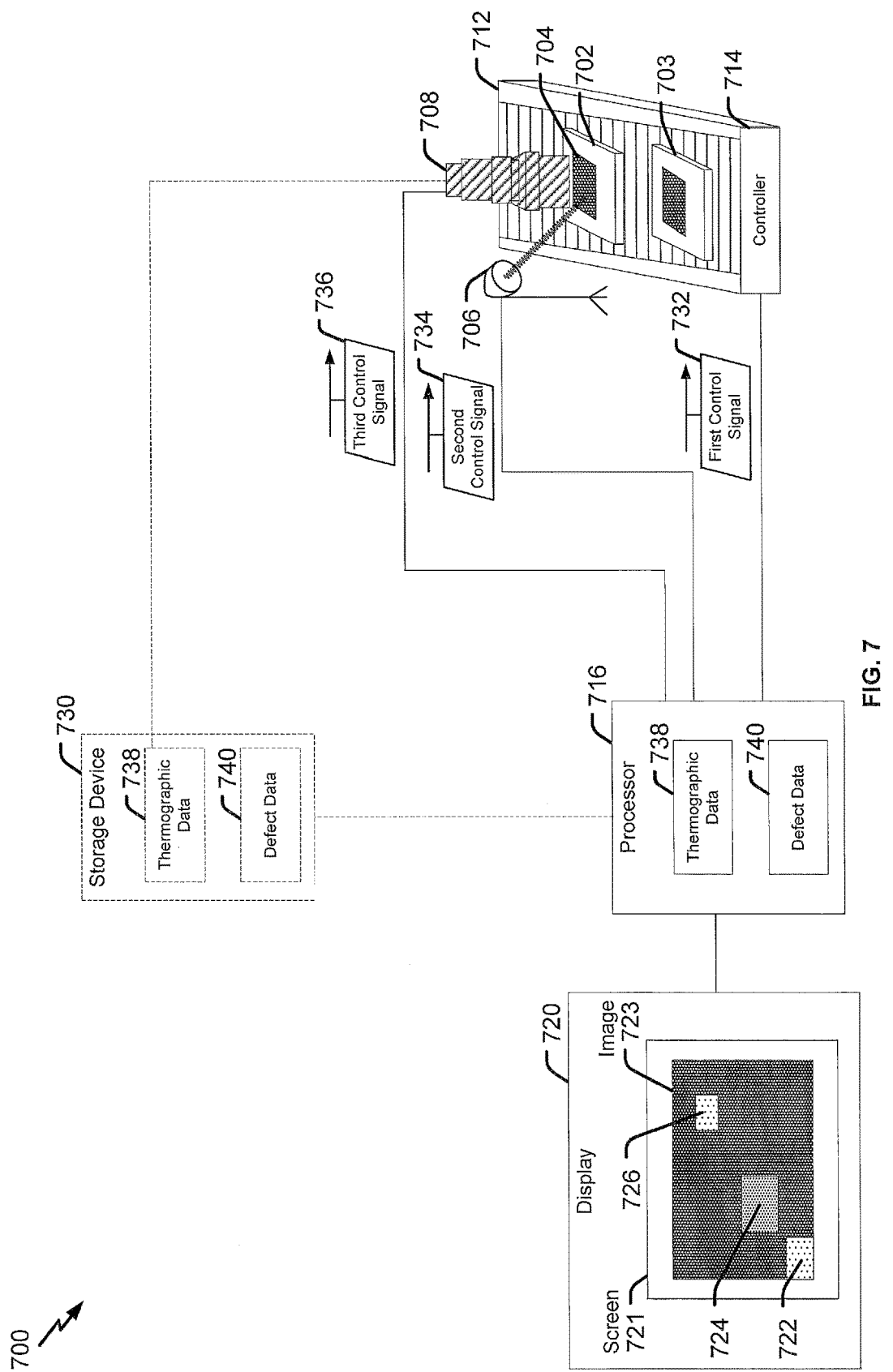
FIG. 7 is a diagram that illustrates another example of a thermographic inspection system.

FIG. 7 illustrates a particular example of a thermographic inspection system 700. The thermographic inspection system 700 may be configured to perform a computer-controlled or automated thermographic inspection on one or more articles using one or more appliques. The thermographic inspection system 700 may include a testing light source 706, a thermographic image capture device 708, a manipulation device 712, a processor 716, and a display device 720.

The processor 716 may be communicatively coupled to the testing light source 706, to the thermographic image capture device 708, to the manipulation device 712, and to the display device 720. For example, the processor 716 may be configured to exchange data, control signals, or both with one or more of the testing light source 706, the thermographic image capture device 708, the manipulation device 712, and the display device 720, via a wired or wireless connection.

In some implementations, the thermographic inspection system 700 optionally includes a storage device 730. The processor 716 and the thermographic image capture device 708 may be communicatively coupled to the storage device 730, via a wired connection, a wireless connection, one or more networks, the Internet, etc.

In some implementations, the thermographic inspection system 700 may also include an application system (configured to apply an applique to an article), an applique removal system (configured to remove the applique from the article), or both, as further described herein. The processor 716 may be communicatively coupled to the application system and to the applique removal system. Although illustrated as separate components in FIG. 7, in other implementations, one or more components may be integrated into a single component. As an illustrative, non-limiting example, the testing light source 706, the thermographic image capture device 708, and the processor 716 may be integrated into a single testing device.

One or more components of the thermographic inspection system 700 may be configured to enable computer-controlled (or automated) performance of a thermographic inspection of one or more articles, such as an illustrative article 702. As an illustrative, non-limiting example, the article 702 may include a component of an aircraft, such as an airfoil, a wing, a control surface, another component, or a portion thereof. Each of the testing light source 706, the thermographic image capture device 708, the manipulation device 712, an optional applique applying device, and an optional applique removal device may be configured to perform one or more operations of the thermographic inspection responsive to control signals from a computer (e.g., from the processor 716).

To illustrate, an application system (e.g., an application device) may be configured to apply an applique, such as an illustrative applique 704, to the article 702 based on control signal(s) from the processor 716. The applique 704 may include or correspond to the applique 104 of FIG. 1, the applique 200 of FIG. 2, the appliques 302 and 304 of FIG. 3, the appliques 402 and 404 of FIG. 4, the applique 500 of FIG. 5, or a combination thereof. The application system may include one or more components that are capable of applying (adhering) the applique 704 to the article 702. To illustrate, the application system may be configured to perform a cleaning process to a target area of the article 702. The target area may be indicated by one or more control signals from the processor 716, and the cleaning process may be initiated by one or more control signals from the processor 716. The application system may also be configured to affix or adhere the applique 704 to the article 702. For example, the application system may be configured to deposit an adhesive to the target area of the article 702 and to adhere the applique 704 to the adhesive. As another example, the application system may be configured to generate static electricity at the target area of the article 702 and to affix the applique 704 to the article 702 using static electricity. In other implementations, the application system may be configured to affix or adhere the applique 704 to the article 702 using other techniques, as described with reference to FIG. 1. The application of the applique 704 may be in accordance with one or more control signals from the processor 716. For example, the one or more control signals may initiate operations at the application system that correspond to a particular type of affixing or adhering (e.g., using static electricity, depositing an adhesive, applying vacuum pressure, etc.). In other implementations, the thermographic inspection system 700 does not include the application system and the applique 704 is applied manually.

The testing light source 706 may be configured to produce electromagnetic radiation (e.g., light) and to direct the electromagnetic radiation towards the applique 704 during the thermographic inspection process. The testing light source 706 may include the testing light source 106 of FIG. 1. The testing light source 706 may be computer-controllable. For example, the testing light source 706 may include one or more components that are configured to adjust an aspect of radiation (e.g., electromagnetic radiation) generation based on one or more control signals from the processor 716. To illustrate, the testing light source 706 may include one or more motors or other components that are configured to adjust a direction of a light source (e.g., an incident angle of the light source) based on a control signal from the processor 716. Additionally or alternatively, the testing light source 706 may be configured to adjust an intensity of the radiation, a duration of the radiation, or both, based on one or more control signals from the processor 716. Additionally or alternatively, the testing light source 706 may include one or more adjustable filters that are configured to adjust a characteristic of the radiation, such as a wavelength of the radiation, and the one or more filters may be adjusted based on one or more control signals from the processor 716.

The thermographic image capture device 708 may be configured to capture (or measure) thermal radiation (e.g., infrared light) emitted by appliques, such as the applique 704. For example, the thermographic image capture device 708, such as the thermographic image capture device 108 of FIG. 1, may include a thermographic camera or a thermographic inspection device, such as a temperature sensor. The thermographic image capture device 708 may be configured to capture thermographic data 738 (associated with a thermographic image) in accordance with one or more control signals from the processor 716. For example, the thermographic image capture device 708 may be configured to initiate or terminate capture of the thermographic data 738 in response to one or more control signals from the processor 716. Additionally or alternatively, the thermographic image capture device 708 may be configured to adjust a frequency associated with capture of the thermographic data 738 based on one or more control signals from the processor 716. Additionally or alternatively, the thermographic image capture device 708 may include one or more motors, actuators, or other components that are configured to adjust a direction or angle of the thermographic image capture device 708 with reference to the article 702 based on one or more control signals from the processor 716. The thermographic image capture device 708 may be configured to generate the thermographic data 738 and to provide the thermographic data 738 to the processor 716. In some implementations, the thermographic image capture device 708 is configured to provide the thermographic data 738 to the storage device 730 (e.g., via one or more networks).

The manipulation device 712 may be configured to manipulate (e.g., orient, move, etc.) articles during the thermographic inspection based on one or more control signals from the processor 716. To illustrate, the manipulation device 712 may include a conveyor, motor(s), actuator(s), lever(s), or other components that are configured to adjust a position, an orientation, or both of one or more articles. Although illustrated as a conveyor system in FIG. 7, in other implementations, the manipulation device 712 may include one or more motorized platforms, one or more arms or levers, one or more wheeled appliances, or other components that are configured to move or orient articles. The manipulation device 712 may be configured to operate based on one or more control signals from the processor 716. For example, the manipulation device 712 may include a controller 714 that is configured to control one or more components of the manipulation device 712 based on one or more control signals from the processor 716. For example, the controller 714 may be configured to cause the manipulation device 712 to align (e.g., adjust a position of) the article 702 with respect to the thermographic image capture device 708 based on a one or more control signals from the processor 716. Additionally or alternatively, the controller 714 may be configured to cause the manipulation device 712 to orient the article 702 based on one or more control signals from the processor 716. Additionally or alternatively, the controller 714 may be configured to cause the manipulation device 712 to move the article 702 outside of an area of focus of the thermographic image capture device 708 and to move a second article 703 into the area of focus (e.g., during a thermographic inspection of the second article 703) based on one or more control signals.

An optional applique removal device may be configured to remove an applique, such the applique 704, from the article 702 based on one or more control signals from the processor 716. The applique removal system may include one or more components that are capable of removing the applique 704 from the article 702. To illustrate, the applique removal system may be configured to discharge static electricity to remove the applique 704, to peel off the applique 704 (e.g., if the applique 704 is affixed due to surface tension), or to apply a solvent to the target area of the article 702 to remove the applique 704 (e.g., if an adhesive is used to adhere the applique 704 to the article 702). The operations initiated by the applique removal system may be based on the one or more control signals from the processor 716. For example, the one or more control signals may indicate operations associated with a particular type of the above-described removal processes. Additionally or alternatively, the applique removal system may be configured to perform a cleaning process on the article 702 after the applique 704 is removed. In some implementations, the applique 704 is a re-usable applique, and the applique 704 may be provided to the application system to be applied to different article to be inspected. In other implementations, the thermographic inspection system 700 does not include an applique removal system and the applique 704 is removed manually.

The processor 716 may be configured to generate control signals to initiate and control a thermographic inspection. The thermographic inspection may be controlled based on user input or based on instructions stored at a memory. For example, the processor 716 may be configured to initiate output of a graphical user interface (GUI) via the display device 720, and a user may use an input device (e.g., a keyboard, a mouse, a touchpad, etc.) to input one or more parameters of the thermographic inspection. Alternatively, the processor 716 may access instructions corresponding to an automated thermographic inspection process, and the processor 716 may provide control signals based on the instructions without input from a user. Additionally, the processor 716 may be configured to receive the thermographic data 738. In a particular implementation, the processor 716 receives the thermographic data 738 from the thermographic image capture device 108 (e.g., via a wired or wireless interface). In another particular implementation, the processor 716 may access the storage device 730 to retrieve the thermographic data 738. The storage device 730 may be an external database or a memory in a different computing device, such as a server. In other implementations, the storage device 730 may be a memory that is integrated in a computer that includes the processor 716.

The processor 716 may be configured to initiate display of a thermographic image 723 at the display device 720. To illustrate, the display device 720 may include a screen 721 that is configured to display one or more thermographic images (e.g., "heat map" images), such as the illustrative thermographic image 723. The thermographic image 723 may include one or more hot spots, such as illustrative hot spots 722, 724, and 726, that are indicative of one or more defects in the article 702. For example, based on image capture setting of the thermographic image capture device 708 or display settings of the display device 720, a hot spot may be a brighter area of the thermographic image 723, as compared to other areas of the thermographic image 723 that are not associated with defects in the article 702. In other implementations, based on image capture setting of the thermographic image capture device 708 or display settings of the display device 720, the thermographic image 723 may include one or more cold spots (e.g., one or more areas that are darker as compared to other areas of the thermographic image 723 that are not associated with defects in the article 702). Image data of the thermographic image 723, or data indicating locations of the hot spots (e.g., locations of defects in the article 702), may be stored as defect data 740. In a particular implementation, the processor 716 may be configured to store the defect data 740 at the storage device 730. The defect data 740 may be compared to other defect data generated during other thermographic inspections of the article 702 to identify changes in the article 702 (e.g., generation of new defects) during a lifetime of the article 702.

During operation, the processor 716 may initiate a thermographic inspection of the article 702. In a particular implementation, the processor 716 may transmit one or more control signals to the application system to cause the applique 704 to be applied to the article 702. Alternatively, the applique 704 may be manually applied to the article 702. The processor 716 may transmit a first control signal 732 to the manipulation device 712. The controller 714 of the manipulation device 712 may cause one or more components of the manipulation device 712 to adjust a position or an orientation of the article 702 based on the first control signal 732. For example, the manipulation device 712 may align a target area of the article 702 (e.g., an area with the applique 704) with the thermographic image capture device 708.

The processor 716 may transmit a second control signal 734 to the testing light source 706 to initiate and/or control one or more aspects of radiation generation, such as electromagnetic radiation generation, during the thermographic inspection. For example, the testing light source 706 may adjust one or more characteristics of the electromagnetic radiation generation (e.g., the light), such as an incident angle, a direction, an intensity, a wavelength, or a combination thereof, based on the second control signal 734. The processor 716 may transmit a third control signal 736 to the thermographic image capture device 708 to initiate and/or control one or more aspects of thermal radiation capture during the thermographic inspection. For example, the thermographic image capture device 708 may adjust a direction or orientation of the thermographic image capture device 708, a frequency of data capture, a duration of data capture, or a combination thereof, based on the third control signal 736. During the inspection process, the thermographic image capture device 708 may capture thermal radiation (e.g., infrared radiation) from the applique 704 and generate the thermographic data 738, such as thermographic image data, based on the captured thermal radiation. The thermographic image capture device 708 may provide the thermographic data 738 (e.g., a thermographic image) to the processor 716. Alternatively, the thermographic image capture device 708 may store the thermographic data 738 (e.g., a thermographic image) at the storage device 730, and the processor 716 may retrieve the thermographic data 738 from the storage device 730.

After capture of the thermographic image is complete, the processor 716 may transmit one or more control signals to the components of the thermographic inspection system 700 to terminate the thermographic inspection. For example, the processor 716 may transmit one or more instructions that cause the testing light source 706 to cease producing light and that cause the thermographic image capture device 708 to cease capturing thermal radiation. Subsequently, the processor 716 may transmit one or more instructions that cause the manipulation device 712 to move the article 702 from a field of view of the thermographic image capture device 708 to an area associated with an applique removal system, and the application removal system may remove the applique 704 from the article 702 (or the applique may be manually removed). If the applique 704 is a re-usable applique, the applique 704 may be stored or may be provided to the application system for use in application to a different article to be inspected.

The processor 716 may analyze the thermographic data 738 to generate the thermographic image 723 and may initiate display (e.g., initiate output) of the thermographic image 723 at the display device 720. Additionally or alternative, if the thermographic data 738 includes thermographic image data (e.g., the thermographic image 723), the processor 716 may analyze the thermographic image data (e.g., the thermographic image 723 and initiate display of the thermographic image 723 via the display device 720.

The thermographic image 723 may indicate one or more hotspots 722, 724, and 726. The one or more hotspots may appear as areas of the thermographic image 723 that are brighter than other areas of the thermographic image 723. The hotspots 722, 724, and 726 may indicate area where defects exist in the article 702. In some implementations, the processor 716 may analyze the thermographic image 723 for the hotspots 722, 724, and 726, and the processor 716 may output a notification of the defect. For example, the processor 716 may cause the display device 720 to outline or highlight the areas of the hotspots 722, 724, and 726. In other implementations, other notifications may be used. Image data of the thermographic image 723 may be stored as the defect data 740, and in some implementations, the defect data 740 may be stored at the storage device 730.

In a particular implementation, the processor 716 may adjust the thermographic image 723 based on one or more thickness measurements of the applique 704. To illustrate, the processor 716 may initiate a measurement (e.g., at a measurement device of the thermographic inspection system 700 or by providing a notification to a user) of a first thickness of the applique 704 before the applique 704 is applied (e.g., affixed or adhered) to the article 702. The processor 716 may initiate a measurement of a second thickness of the applique 704 after the applique 704 is applied to the article 702. After the measurements are determined, the processor 716 may compare the first thickness to the second thickness to determine a change in thickness of the applique 704. The thermographic image 723 may be adjusted based on the change in thickness. For example, the processor 716 may adjust a temperature indicated by a portion of the thermographic image 723 (e.g., a brightness of an area of the thermographic image 723) based on the change in thickness. To illustrate, if the second thickness is less than the first thickness, the applique 704 may be expected to emit additional thermal radiation, which would result in a hot spot being displayed in the thermographic image 723 even if a defect did not exist in the article 702. Thus, the processor 716 may reduce a brightness of an area of the thermographic image 723 that corresponds to an area where the second thickness of the applique 704 is less than the first thickness.

Thus, the thermographic inspection system 700 of FIG. 7 enables performance of a computer-controlled thermographic inspection of articles using appliques. Because the inspection process is automated (or nearly automated), cost and efficiency improvements may be obtained as compared to a manual thermographic inspection process. Additionally, the thermographic data 738 (e.g., the thermographic image 723) that is generated by the thermographic inspection may be analyzed by a computer (e.g., the processor 716) to indicate areas of an article where defects exist using a simple visual image (e.g., the thermographic image 723).

Figure 8:
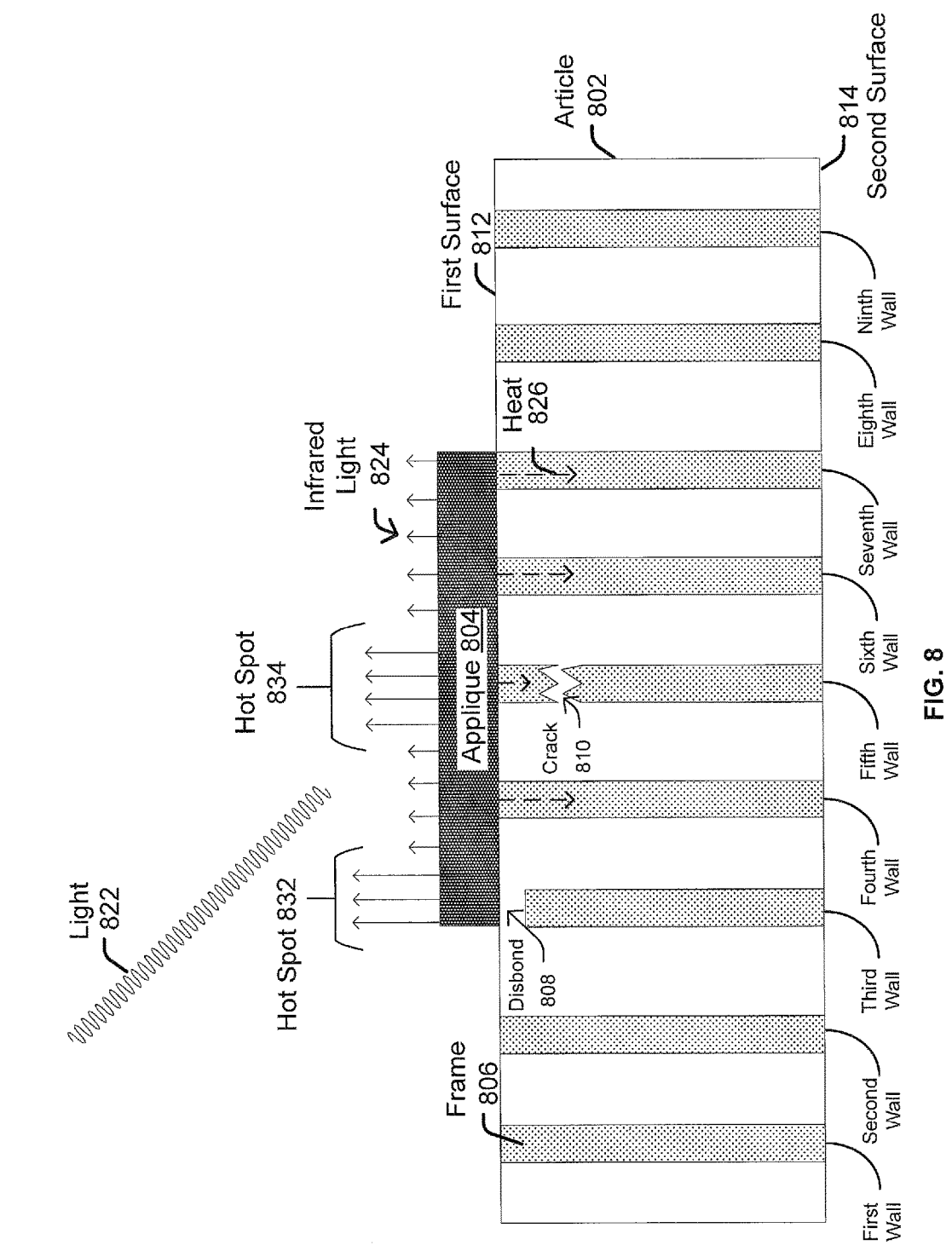
FIG. 8 is a diagram that illustrates an example of use of an applique to identify a defect of a component.

FIG. 8 illustrates an example 800 of use of an applique 804 to identify a defect of a component. The applique 804 may include or correspond to the applique 104 of FIG. 1, the applique 200 of FIG. 2, the appliques 302, 304 of FIG. 3, the appliques 402, 404 of FIG. 4, the applique 500 of FIG. 5, the applique 600 of FIG. 6, the applique 704 of FIG. 7, or a combination thereof.

The applique 804 may be used for thermographic inspection of one or more articles, such as an article 802. The article 802 may include the article 102 of FIG. 1 or one of the articles 702, 703 of FIG. 7. The article 802 may include a first surface 812, a second surface 814, and a frame 806 positioned between the first surface 812 and the second surface 814. In a particular implementation, the frame 806 correspond to an aluminum honeycomb core and may include a plurality of thin walls extending from the first surface 812 to the second surface 814. As illustrated in FIG. 8, the article 802 includes a disbond 808 between the frame 806 (e.g., a third thin wall of the frame 806) and the first surface 812 of the article 802 and includes a crack 810 in a portion of the frame 806 (e.g., a fifth thin wall of the frame 806).

During operation of a thermographic inspection, the applique 804 may be removably coupled to a test area of the first surface 812 of the article 802. As illustrated, the applique 804 is positioned over multiple walls of the frame 806. Light 822 may be applied to the applique 804 from a testing light source, such as a testing light source 106 of FIG. 1 or the testing light source 706 of FIG. 7. A portion of the light 822 may be absorbed by the applique 804 to generate thermal energy. The applique 804 may transfer a first portion of the thermal energy as heat 826 to the first surface of the article 802. The heat 126 may be transferred from the first surface 812 of the article 802 to the frame 806. Defects in the frame 806, such as the disbond 808 and the crack 810, may interfere with transfer of the heat 826 from the first surface 812 to the frame 806. As illustrated in FIG. 8, more heat 126 is transferred by the applique 804 and the first surface 812 to each of a fourth thin wall, a six thin wall, and the seventh thin wall than heat 126 transferred by the applique 804 and the first surface 812 to each of the third thin wall and to the fifth thin wall.

The applique 804 may transfer (e.g., emit) a second portion of the thermal energy as infrared light 824. For a given area of the applique 804, an amount of infrared light 824 emitted (e.g., the second portion of the thermal energy) may be dependent on an amount of the heat 126 transferred (e.g., the first portion of the thermal energy) to the article 802. To illustrate, the less heat 126 transferred to the article 802, the more of the thermal energy is retained by the applique 804 and the more infrared light 824 is emitted. Thus, a first portion of the applique 804 positioned above a defect may emit more infrared light 824 than a second portion of the applique 804 that is not positioned above a defect. As illustrated in FIG. 8, hot spots 832, 834 may form in (or on) the applique 804 and may emit a greater amount of infrared light 824 than other (e.g., surrounding) areas of the applique. The hot spots 832, 834 may correspond to the defects, e.g., the disbond 808 and the crack 810 respectively.

The infrared light 824 (and the hot spots 832, 834) may be received and captured by a thermographic image capture device, such as the thermographic image capture device 108 of FIG. 1. The thermographic image capture device may generate thermographic image data based on the captured infrared light 824 and may output a thermographic image. The thermographic image may indicate the hot spots 832, 834.

Figure 9:
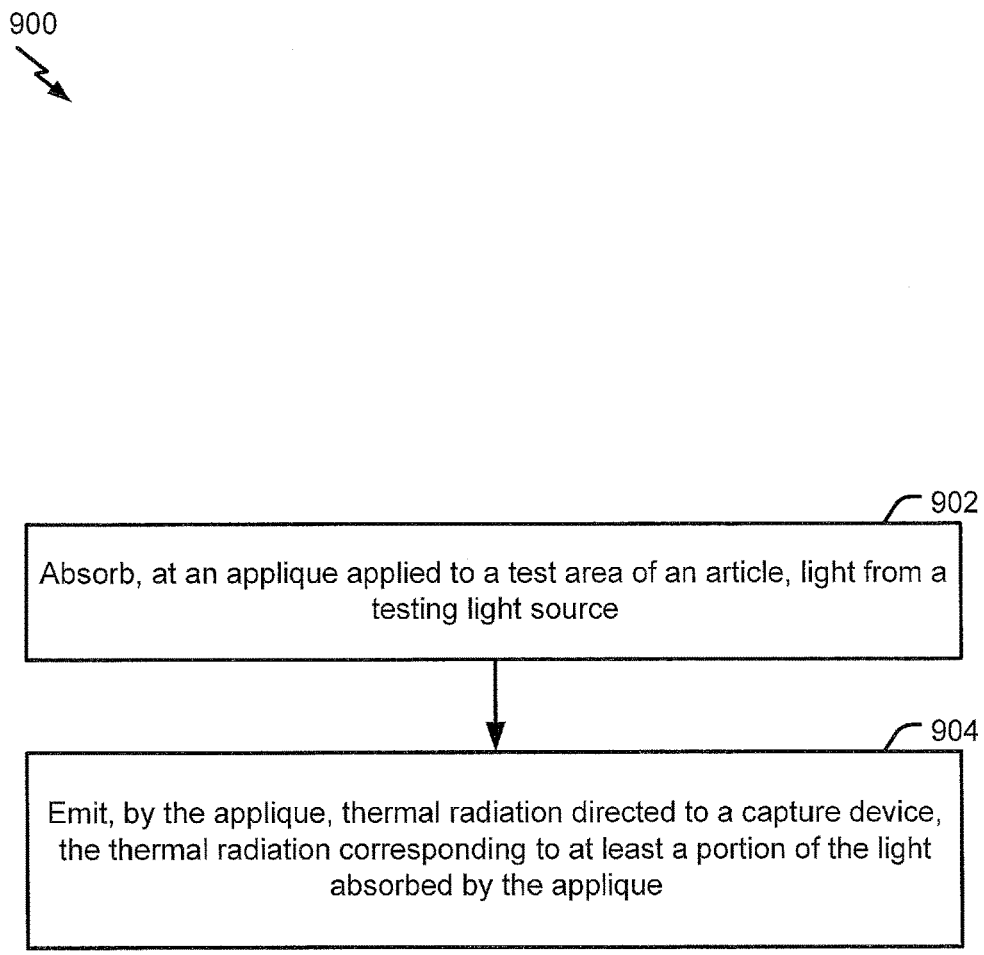
FIG. 9 is a flow chart of an example of a method of thermographic inspection.

FIG. 9 illustrates a particular example of a method 900 of method of performing a thermographic inspection. The method 900 may be performed by a thermographic inspection system, such as the thermographic inspection system 100 (e.g., the applique 104) of FIG. 1, the system 700 of FIG. 7, or a combination thereof, as illustrative, non-limiting examples.

The method 900 includes, at 902, absorbing, at an applique applied to a test area of an article, light form a testing light source. For example, the applique may include or correspond to the applique 104 of FIG. 1, the applique 200 of FIG. 2, the appliques 302, 304 of FIG. 3, the appliques 402, 404 of FIG. 4, the applique 500 of FIG. 5, the applique 600 of FIG. 6, the applique 704 of FIG. 7, or the applique 804 of FIG. 8. In some implementations, the article may include a metallic component of vehicle. The article may include or correspond to the article 102 of FIG. 1, the article 702 of FIG. 7, or the article 802 of FIG. 8. The testing light source may include an incandescent light source, a laser device, a flashlamp or a flashtube. For example, the testing light source may include the testing light source 106 of FIG. 1 or the testing light source 706 of FIG. 7. The light may include or correspond to the light 122 of FIG. 1, the light 344 of FIG. 3, the light 424 of FIG. 4, or the light 822 of FIG. 8.

The method 900 includes, at 904, emitting, by the applique, thermal radiation directed to a capture device. The thermal radiation corresponds to at least a portion of the light absorbed by the applique. For example, the thermal radiation may include or correspond to the infrared light 124 of FIG. 1 or the infrared light 824 of FIG. 8. The capture device may include a thermographic image capture device, such as the thermographic image capture device 108 of FIG. 1 or the thermographic image capture device 708 of FIG. 7.

In some implementations, the light has wavelengths in a visible light spectrum and the capture device (e.g., thermographic image capture device) captures infrared light having wavelengths in a near infrared light spectrum. The capture device may generate a thermographic image based on the thermal radiation. The thermographic image may be analyzed for a potential defect that may be identified based on one or more hot spots (e.g., areas having increased temperatures) as indicated by the thermographic image.

The applique may include a first surface and a second surface. The first surface may include a cavity or a microstructure. A portion of the light may be absorbed by the cavity or the microstructure of the first surface of the applique. The second surface may be coupled to the article. In some implementations, the method 900 may include transferring, from a second surface of the applique to the test area, thermal energy by conduction. In such implementation, the thermal radiation emitted by the applique is based on the thermal energy transferred by conduction.

In some implementations, the method 900 may include, prior to absorbing the light, applying the applique to the test area of the article via surface tension, static electricity, or vacuum pressure. After the applique is applied to the article, the light may be applied to the applique from the testing light source. After completion of the thermographic inspection of the test area, the applique may be removed from the test area of the article. In some implementations, the applique may be reusable. Accordingly, after the applique is removed from the test area, the applique may be applied to a second test area of the article and a second thermographic inspection associated with the second test area may be performed. Alternatively, after the applique is removed from the test area, the applique may be applied to a test area of a second article and another thermographic inspection associated with the test area of the second article may be performed.

In some implementations, the thermally conductive material has a light absorption coefficient and a light reflection coefficient, wherein the light absorption coefficient is greater than the light reflection coefficient. In a particular implementation, the thermally conductive material may include matte black finish.

The method 900 may enable portable non-destructive testing of an article. The method 900 may enable thermographic inspection on materials with a high reflection coefficient, such as shiny glossy surfaces, bare metal surfaces, white colored surfaces, etc. By utilizing removable appliques, the method 900 may reduce surface preparation and cleaning time as compared to brush on or spray on paint and coatings. By reducing surface preparation and cleaning time, inspection times may are shortened and cost savings may be achieved from reduced labor and material costs. For example, material costs may be reduced as reusable appliques may replace paint, coatings, solvents, and cleaners, or reduce an amount of paint, coatings, solvents, and cleaners.

By including a plurality of features (e.g., cavities, microstructures, nanoparticles, etc.) in the applique, the applique may provide higher quality thermographic images than conventional planar or colorized appliques. For example, the plurality of features may increase absorptivity and emissivity of the applique and may decrease reflectivity. Accordingly, a signal to noise ratio of the thermographic images may be increased which may result in higher quality thermographic images that enable an increased detection of defects in an article.

Figure 10:
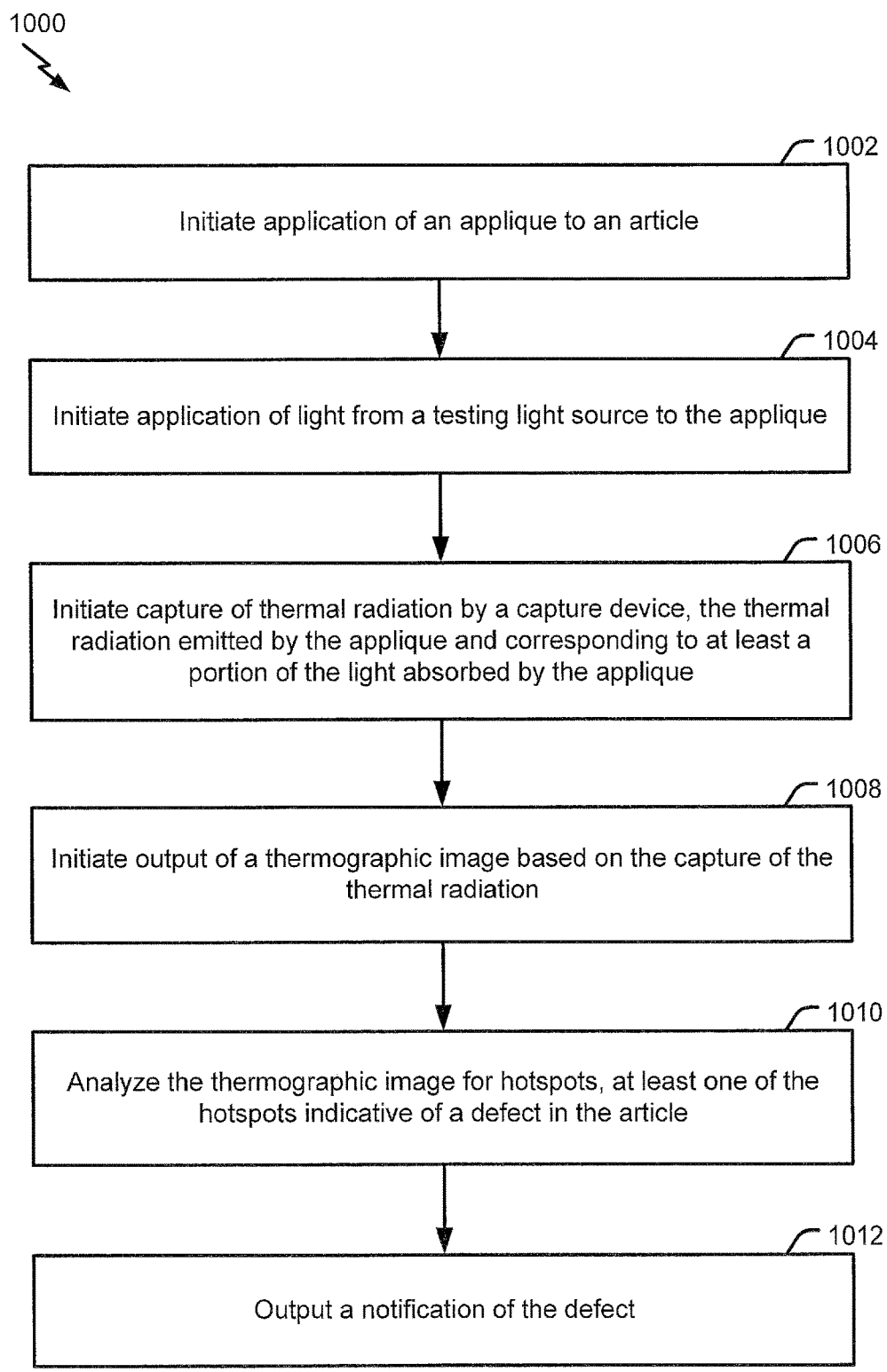
FIG. 10 is a flow chart of another example of a method of thermographic inspection.

FIG. 10 illustrates a particular example of a method 1000 performing a thermographic inspection. The method 1000 may be performed by a thermographic inspection system, such as the thermographic inspection system 100 of FIG. 1, the system 700 (e.g., the processor 716) of FIG. 7, or a combination thereof, as illustrative, non-limiting examples.

The method 1000 may include, at 1002, initiating application of an applique to an article. For example, the applique may include or correspond to the applique 104 of FIG. 1, the applique 200 of FIG. 2, the appliques 302, 304 of FIG. 3, the appliques 402, 404 of FIG. 4, the applique 500 of FIG. 5, the applique 600 of FIG. 6, the applique 704 of FIG. 7, or the applique 804 of FIG. 8. The article may include or correspond to the article 102 of FIG. 1, the article 702 of FIG. 7, or the article 802 of FIG. 8. The applique may be applied by adhesives, intermolecular surface tension, electrostatic force, vacuum pressure, or a combination thereof.

The method 1000 may include initiating application of light from a testing light source to the applique, at 1004. For example, the testing light source may include the testing light source 106 of FIG. 1 or the testing light source 706 of FIG. 7. The light may include or correspond to the light 122 of FIG. 1, the light 344 of FIG. 3, the light 424 of FIG. 4, or the light 822 of FIG. 8. Alternatively, the method 1000 may include generating heat from a heat generation layer, such as the heat generation layer 604 of FIG. 6.

The method 1000 may include, at 1006, initiating capture of thermal radiation by a capture device. The thermal radiation emitted by the applique and corresponding to at least a portion of the light absorbed by the applique. The capture device may include a thermographic image capture device, such as the thermographic image capture device 108 of FIG. 1 or the thermographic image capture device 708 of FIG. 7. In some implementations, the light has wavelengths in a visible light spectrum and the capture device (e.g., thermographic image capture device) captures infrared light having wavelengths in a near infrared light spectrum.

The method 1000 may include initiating output of a thermographic image based on the capture of the thermal radiation, at 1008. For example, the thermographic image may include the thermographic image 723 of FIG. 7. In some implementations, the method 1000 may include initiating transmission of the thermographic image to a remote storage device, such as the storage device 730 of FIG. 7.

The method 1000 may include, at 1010, analyzing the thermographic image for hotspots, at least one of the hotspots indicative of a defect in the article and, at 1012, outputting a notification of the defect (e.g., a potential defect). For example, the notification may be output via a display device, such as the display device 720 of FIG. 7. Analyzing the thermographic image may include identifying one or more hot spots (or cool spots) that indicate a defect. Additionally or alternatively, analyzing the thermographic image may include comparing the thermographic image to a previously captured thermographic image of the same portion of the article, comparing the thermographic image to structural diagram (e.g., a blueprint) of the article, or a combination thereof, as illustrative, non-limiting examples.

In some implementations, after identifying a potential defect, the method 1000 may include removing the applique for a portion of the article that corresponds to the potential defect and applying a coating (e.g., lampblack or flat black paint) to the portion of the article. After the coating is applied, second light from the testing light source to the coating and a second thermographic image may be captured of the coating. The second thermographic image may be analyzed to verify the defect.

In some implementations, prior to applying the light, the method 1000 may include applying the applique to a test area of the article. The applique may be applied such that at least one corner or edge is not adhered to a surface of the test area. After capturing the thermographic image while the applique is adhered to the test area, the applique may be removed. For example, the applique may be removed by peeling the applique from the surface at approximately a first angle relative to the surface by the at least one corner or edge using a peel test instrument. In some implementations, the applique is removed independent of a solvent.

In some implementations, the applique may be reusable. For example, after the applique is removed from the test area, the applique may be applied to another test area of the same article or of a different article. To illustrate, the applique may be applied to another surface of the article, to a surface of a second article, or both.

In some implementations, the method 1000 may include initiating measurement of a first thickness of the applique before applying the applique to the article and initiating measurement of a second thickness of the applique after applying the applique to the article. The first thickness may be compared to the second thickness to determine a change in thickness of the applique. The thermographic image may be analyzed or adjusted based on the change in thickness. For example, a temperature indicated by a portion of the thermographic image may be adjusted based on the change in thickness. Additionally or alternatively, a notification may be generated based on the change in thickness. The notification may indicate the change in thickness and a corresponding area where the change in thickens occurred. As thermal conductivity is based on the thickness of the applique, the change in thickness may affect the thermal conductivity of the applique and thus the amount of thermal radiation emitted. To illustrate, if the change in thickness is negative, the notification may be indicative of areas where thermal conductivity may be increased and artificial hot spots (e.g., hot spots not indicative of a defect) may occur.

In some implementations, the method 1000 may include calibration and adjustment operations. For example, the method 1000 may include initiating measurement of a gloss or a matte quality of the applique. To illustrate, a specular gloss instrument may measure the gloss or the matte quality of the applique. The method 1000 may further include adjusting an angle of the light based on the change in thickness, the gloss quality, the matte quality, or a combination thereof, of the applique.

The method 1000 may enable portable non-destructive testing of an article. The method 1000 may enable computer-controlled or automated thermographic inspection of materials with a high reflection coefficient, such as shiny glossy surfaces, bare metal surfaces, white colored surfaces, etc. By utilizing removable appliques, the method 1000 may reduce surface preparation and cleaning time as compared to brush on or spray on paint and coatings. By reducing surface preparation and cleaning time, inspection times may are shortened and cost savings may be achieved from reduced labor and material costs. For example, material costs may be reduced as reusable appliques may replace paint, coatings, solvents, and cleaners, or reduce an amount of paint, coatings, solvents, and cleaners.

By including a plurality of features (e.g., cavities, microstructures, nanoparticles, etc.) in the applique, the applique may provide higher quality thermographic images than conventional planar or colorized appliques. For example, the plurality of features may increase absorptivity and emissivity of the applique and may decrease reflectivity. Accordingly, a signal to noise ratio of the thermographic images may be increased which may result in higher quality thermographic images that enable an increased detection of defects in an article.

The method 1000 of FIG. 10 may be initiated or controlled by an application-specific integrated circuit (ASIC), a processing unit, such as a central processing unit (CPU), a controller, another hardware device, a firmware device, a field-programmable gate array (FPGA) device, or any combination thereof. As an example, the method 1000 of FIG. 10 can be initiated or controlled by one or more processors, such as one or more processors included in or coupled to a controller of a thermographic inspection system (e.g., a thermographic inspection device). In some implementations, a portion of one of the methods FIGS. 9-10 may be combined with a second portion of one of the methods of FIGS. 9-10. Additionally, one or more operations described with reference to the FIGS. 9-10 may be optional, may be performed at least partially concurrently, and/or may be performed in a different order than shown or described.

Figure 11:
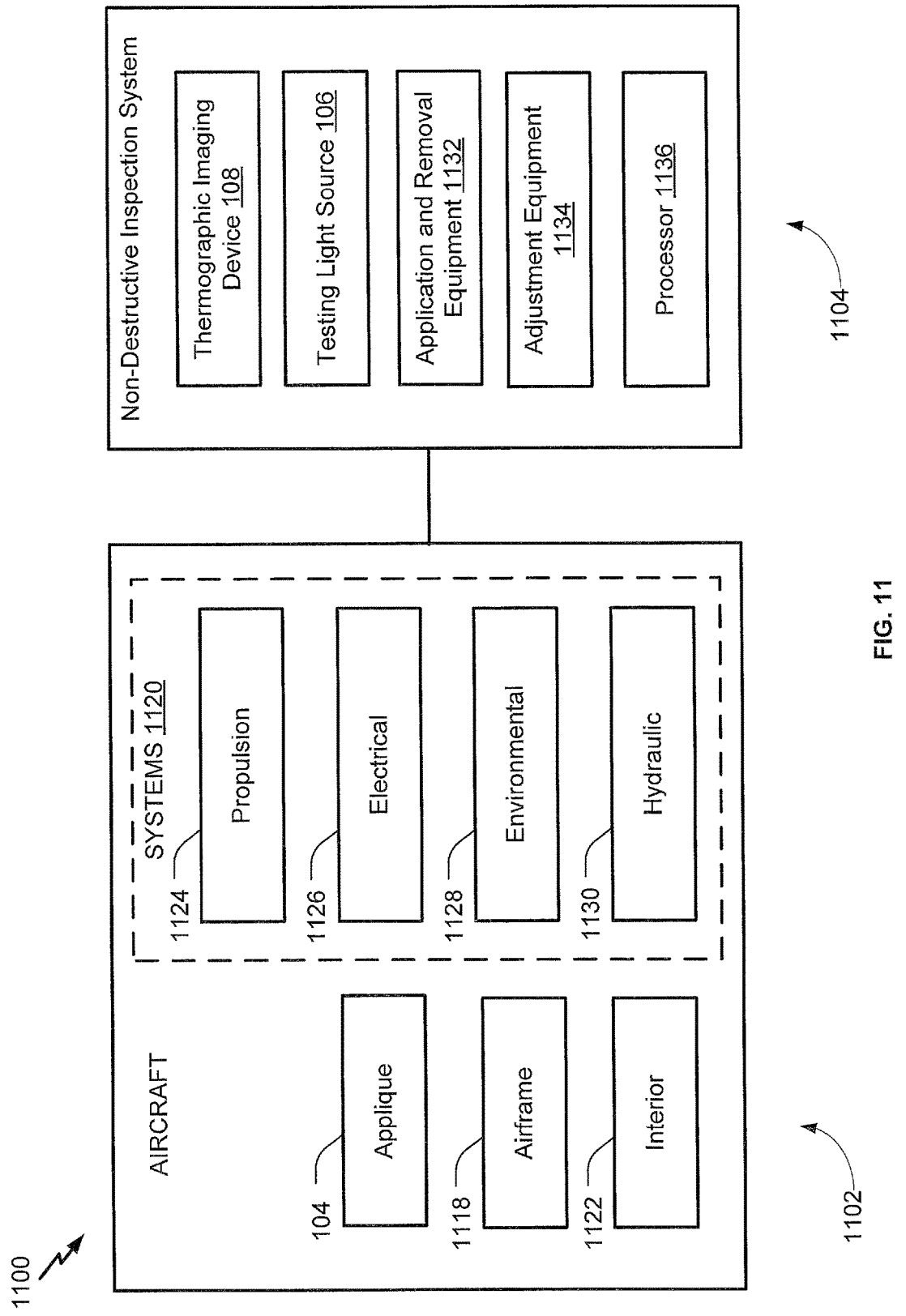
FIG. 11 is a block diagram of an illustrative implementation of a vehicle and a thermographic inspection system.

Referring to FIG. 11, a block diagram of an illustrative implementation of a vehicle 1102 coupled to a non-destructive inspection system 1104 is shown and designated 1100. The vehicle 1102 may include an aircraft, an airship, or another vehicle, as illustrative, non-limiting examples. The vehicle 1102 may be manned or unmanned (e.g., a drone or an unmanned aerial vehicle (UAV). To illustrate, the vehicle 902 may include an aircraft, as an illustrative, non-limiting example. The vehicle 1102 may include a component or article, such as the article 102 of FIG. 1 or the article 802 of FIG. 1, that is subjected to a thermographic inspection using the non-destructive inspection system 1104.

As shown in FIG. 11, the vehicle 1102 (e.g., an aircraft) may include an airframe 1118, an interior 1122, and a plurality of systems 1120. The plurality of systems 1120 may include one or more of a propulsion system 1124, an electrical system 1126, an environmental system 1128, or a hydraulic system 1130. Additionally or alternatively, the plurality of systems 1120 may include any number of other systems, such as a control system or a communications system. For example, the communications system may be configured to communicate with the non-destructive inspection system 1104 via a wired connection, a wireless connection, or both. The communications system may include a transceiver, one or more antennas, and a communication controller. The plurality of systems 1120 may include one or more memories and one or more processors. The one or more processors may be configured to execute computer-executable instructions (e.g., a program of one or more instructions) stored in the one or more memories. The instructions, when executed, cause the one or more processors to perform operations associated with the plurality of systems 1120.

In some implementations, the vehicle 1102 may include the applique 104 that is affixed to a portion of the vehicle as part of a thermographic inspection performed using the non-destructive inspection system. The non-destructive inspection system 1104 may include the thermographic image capture device 108, the testing light source 106, the application and removal equipment 1132, the adjustment equipment 1134, and a processor 1136. Additionally or alternatively, the non-destructive inspection system may include a memory configured to store data (e.g., thermographic data), computer-executable instructions, or a combination thereof. For example, the memory may include or correspond to the storage device 710 of FIG. 7. In some implementations, the processor may be configured to execute the computer-executable instructions (e.g., a program of one or more instructions) stored at the memory of the non-destructive inspection system 1104. The instructions, when executed by the processor 1136, may cause the processor 1136 to perform operations associated with the non-destructive inspection system 1104 to perform a thermographic inspection of a portion of the vehicle 1102 that corresponds to the applique 104.

The illustrations of the examples described herein are intended to provide a general understanding of the structure of the various implementations. The illustrations are not intended to serve as a complete description of all of the elements and features of apparatus and systems that utilize the structures or methods described herein. Many other implementations may be apparent to those of skill in the art upon reviewing the disclosure. Other implementations may be utilized and derived from the disclosure, such that structural and logical substitutions and changes may be made without departing from the scope of the disclosure. For example, method operations may be performed in a different order than shown in the figures or one or more method operations may be omitted. Accordingly, the disclosure and the figures are to be regarded as illustrative rather than restrictive.

Moreover, although specific examples have been illustrated and described herein, it should be appreciated that any subsequent arrangement designed to achieve the same or similar results may be substituted for the specific implementations shown. This disclosure is intended to cover any and all subsequent adaptations or variations of various implementations. Combinations of the above implementations, and other implementations not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single implementation for the purpose of streamlining the disclosure. Examples described above illustrate but do not limit the disclosure. It should also be understood that numerous modifications and variations are possible in accordance with the principles of the present disclosure. As the following claims reflect, the claimed subject matter may be directed to less than all of the features of any of the disclosed examples. Accordingly, the scope of the disclosure is defined by the following claims and their equivalents.

What is claimed is:

1. A thermal transfer applique for attachment to an object, the thermal transfer applique comprising:
a thermally conductive material configured to generate thermal energy upon exposure to light, the thermally conductive material having a first surface and a second surface, the first surface configured to enable transfer of thermal energy to the object; and
a plurality of light absorbing cavities formed in the second surface of the thermally conductive material, wherein at least a portion of the second surface opposes the first surface.

2. The thermal transfer applique of claim 1, wherein each of the plurality of light absorbing cavities has a diameter that is less than a depth of the light absorbing cavity, and wherein each of the plurality of light absorbing cavities has a circular shape or a hexagonal shape.

3. The thermal transfer applique of claim 1, wherein at least one of the plurality of light absorbing cavities extends to the first surface.

4. The thermal transfer applique of claim 1, wherein the plurality of light absorbing cavities are arranged in a tessellated pattern, a rectangular pattern, or both.

5. The thermal transfer applique of claim 1, wherein the thermally conductive material has a light absorption coefficient and a light reflection coefficient, wherein the light absorption coefficient is greater than the light reflection coefficient.

6. The thermal transfer applique of claim 1, wherein the thermally conductive material comprises vinyl, a polymer, a carbon fiber material, or a combination thereof.

7. The thermal transfer applique of claim 1, further comprising an adhesive layer coupled to the first surface, wherein the first surface and the second surface are part of a thermal transfer layer.

8. A thermal transfer applique for attachment to an object, the thermal transfer applique comprising:
   a thermally conductive material configured to generate thermal energy upon exposure to light, the thermally conductive material having a first surface and a second surface and including a plurality of microstructures extending from the second surface, the thermally conductive material having a light absorption coefficient and a light reflection coefficient, wherein the light absorption coefficient is greater than the light reflection coefficient, wherein the first surface of the thermally conductive material is configured to enable transfer of thermal energy to the object, and wherein at least a portion of the second surface opposes the first surface.

9. The thermal transfer applique of claim 8, wherein the plurality of microstructures includes one or more grooves, cones, pyramids, tubes, cylinders, or a combination thereof.

10. The thermal transfer applique of claim 8, wherein the plurality of microstructures are arranged in a tessellated pattern, a rectangular pattern, or both, wherein the plurality of microstructures comprise rectangular pyramids, and wherein the rectangular pyramids are transparent or translucent.

11. The thermal transfer applique of claim 8, wherein the first surface and the second surface define one or more air vents, wherein the one or more air vents are dispersed among the plurality of microstructures.

12. The thermal transfer applique of claim 8, further comprising an adhesive material disposed on the first surface, such that the first surface is attachable to a metallic article under test.

13. The thermal transfer applique of claim 8, wherein the thermally conductive material has a first thermal coefficient in a first direction and a second thermal coefficient in a second direction, the first thermal coefficient greater than the second thermal coefficient, and wherein the first surface is attachable to a surface of an airfoil, a fuselage, or a control surface of an aircraft.

14. A method of testing comprising:
   absorbing, at an applique applied to a test area of an article, light from a testing light source, the applique including a thermally conductive material; and
   emitting, by the applique, thermal radiation directed to a capture device, the thermal radiation corresponding to at least a portion of the light absorbed by the applique.

15. The method of claim 14, wherein the capture device comprises a thermographic image capture device, and wherein the testing light source comprises an incandescent light source, a laser device, a flashlamp or a flashtube.

16. The method of claim 15, wherein the light has wavelengths in a visible light spectrum, and wherein the thermographic image capture device captures infrared light having wavelengths in a near infrared light spectrum.

17. The method of claim 14, wherein a portion of the light is absorbed by a cavity or a microstructure of a first surface of the applique.

18. The method of claim 17, further comprising transferring, from a second surface of the applique to the test area, thermal energy by conduction, wherein the thermal radiation emitted by the applique is based on the thermal energy transferred by conduction.

19. The method of claim 14, wherein the capture device generates a thermographic image based on the thermal radiation, wherein the thermographic image is analyzed for one or more hot spots, and wherein at least one of the one or more hot spots indicates a potential defect.

20. The method of claim 14, further comprising applying the applique to the test area of the article via surface tension, static electricity, or vacuum pressure, wherein the article is a metallic component of a vehicle.

* * * * *